US 6,558,623 B1

(12) United States Patent
Ganz et al.

(10) Patent No.: US 6,558,623 B1
(45) Date of Patent: May 6, 2003

(54) MICROARRAY DISPENSING WITH REAL-TIME VERIFICATION AND INSPECTION

(75) Inventors: Brian L. Ganz, Carlsbad, CA (US); Mandel W. Mickley, Oceanside, CA (US); John Andrew Moulds, Encinitas, CA (US); Christopher T. Brovold, Carlsbad, CA (US)

(73) Assignee: RoboDesign International, Inc., Carlsbad, CA (US)

( * ) Notice: Subject to any disclaimer, the term of this patent is extended or adjusted under 35 U.S.C. 154(b) by 0 days.

(21) Appl. No.: 09/611,256

(22) Filed: Jul. 6, 2000

(51) Int. Cl.⁷ .................. B32B 27/04; B32B 27/12; B32B 5/02; G01N 21/00; G01N 31/00; B01L 3/02; B01L 15/06; B01L 33/00; G06K 9/00; G01B 11/14

(52) U.S. Cl. .................. 422/63; 422/68.1; 422/100; 422/105; 73/863.01; 73/864.01; 73/864.11; 73/864.25; 382/133; 356/237.1; 356/237.6; 356/614

(58) Field of Search .................. 422/100, 105, 422/63, 68.1; 73/863.01, 864.01, 864.11, 864.25; 141/119, 57, 61; 382/133, 134; 356/614, 237.1, 237.6

(56) References Cited

U.S. PATENT DOCUMENTS

| 4,378,333 A | * | 3/1983 | Laipply ..................... 422/100 |
| 5,059,393 A | * | 10/1991 | Quenin et al. ............... 422/64 |
| 5,104,621 A | * | 4/1992 | Pfost et al. .................. 422/67 |
| 5,425,918 A | * | 6/1995 | Healy et al. ................. 422/64 |
| 5,601,980 A | * | 2/1997 | Gordon et al. ................ 435/6 |
| 5,655,029 A | * | 8/1997 | Rutenberg et al. .......... 382/133 |
| 5,715,327 A | * | 2/1998 | Wilhelm et al. ............. 382/128 |
| 5,812,692 A | * | 9/1998 | Rosenlof et al. ............ 382/133 |
| 5,830,413 A | * | 11/1998 | Lang et al. ................. 422/100 |
| 5,879,628 A | * | 3/1999 | Ridgeway et al. ............ 422/73 |
| 5,948,359 A | * | 9/1999 | Karla et al. .................. 422/65 |
| 5,958,342 A | * | 9/1999 | Gamble et al. .............. 422/100 |
| 6,024,925 A | * | 2/2000 | Little et al. ................. 422/100 |
| 6,026,174 A | * | 2/2000 | Palcic et al. |
| 6,078,681 A | * | 6/2000 | Silver ......................... 382/133 |
| 6,110,426 A | * | 8/2000 | Shalon et al. .............. 422/68.1 |
| 6,122,396 A | * | 9/2000 | King et al. ................. 382/133 |
| 6,130,956 A | * | 10/2000 | Butterworth et al. ....... 382/100 |
| 6,215,892 B1 | * | 4/2001 | Douglass et al. |
| 6,219,442 B1 | * | 4/2001 | Harper et al. |
| 6,243,486 B1 | * | 6/2001 | Weiss .......................... 382/133 |

(List continued on next page.)

*Primary Examiner*—Jill Warden
*Assistant Examiner*—Brian R Gordon
(74) *Attorney, Agent, or Firm*—John R. Ross; John R. Ross, III

(57) ABSTRACT

A microarrayer for spotting solution onto slides in an automated microarray dispensing device. Elements of the present invention include: at least one dispense head for spotting the slides, at least one light source capable of illuminating the slides, at least one camera operating in conjunction with the at least one light source. The at least one camera is capable of acquiring and transmitting slide image data to a computer. The computer is programmed to receive the slide image data and analyze it. The computer will then generate post analysis data based on the analysis of the slide image data. The post analysis data is available for improving the spotting of the solution onto the slides. In a preferred embodiment, the slide image data includes information relating to slide alignment, information relating to spot quality, and slide identification information. In a preferred embodiment, the analysis of the information relating to slide alignment enables the computer to make automatic adjustments to the relative positions of the at least one dispense head and the slides to increase the accuracy of the spotting. In a preferred embodiment, the analysis of the information relating to spot quality identifies a spot as pass or fail. An operator is then able to rework the spot. In a preferred embodiment, the analysis of the slide identification information enables the computer to track each slide.

25 Claims, 42 Drawing Sheets

U.S. PATENT DOCUMENTS

| | | | |
|---|---|---|---|
| 6,246,785 B1 * | 6/2001 | Molnar et al. | |
| 6,252,979 B1 * | 6/2001 | Lee et al. | |
| 6,259,807 B1 * | 7/2001 | Ravkin | 382/133 |
| 6,263,095 B1 * | 7/2001 | Rushbrooke et al. | |
| 6,269,846 B1 * | 8/2001 | Overbeck et al. | 141/1 |
| 6,271,022 B1 * | 8/2001 | Bochner | |
| 6,275,777 B1 * | 8/2001 | Shimizu | 702/30 |
| 6,327,377 B1 * | 12/2001 | Rutenberg et al. | 382/133 |
| 6,330,349 B1 * | 12/2001 | Hayes et al. | |
| 6,349,144 B1 * | 2/2002 | Shams | 382/129 |
| 6,351,573 B1 * | 2/2002 | Schneider | 382/294 |
| 6,362,004 B1 * | 3/2002 | Noblett | 436/43 |
| 6,381,353 B1 * | 4/2002 | Weiss | 382/133 |
| 6,418,236 B1 * | 7/2002 | Ellis et al. | 382/128 |
| 6,453,060 B1 * | 9/2002 | Riley et al. | 382/133 |
| 6,466,690 B2 * | 10/2002 | Bacus et al. | 382/133 |
| 2001/0017938 A1 * | 8/2001 | Kerschmann et al. | 382/133 |
| 2002/0019003 A1 * | 2/2002 | Haase et al. | |
| 2002/0076092 A1 * | 6/2002 | Ellis et al. | 382/133 |
| 2002/0081013 A1 * | 6/2002 | Raz | 382/133 |

* cited by examiner

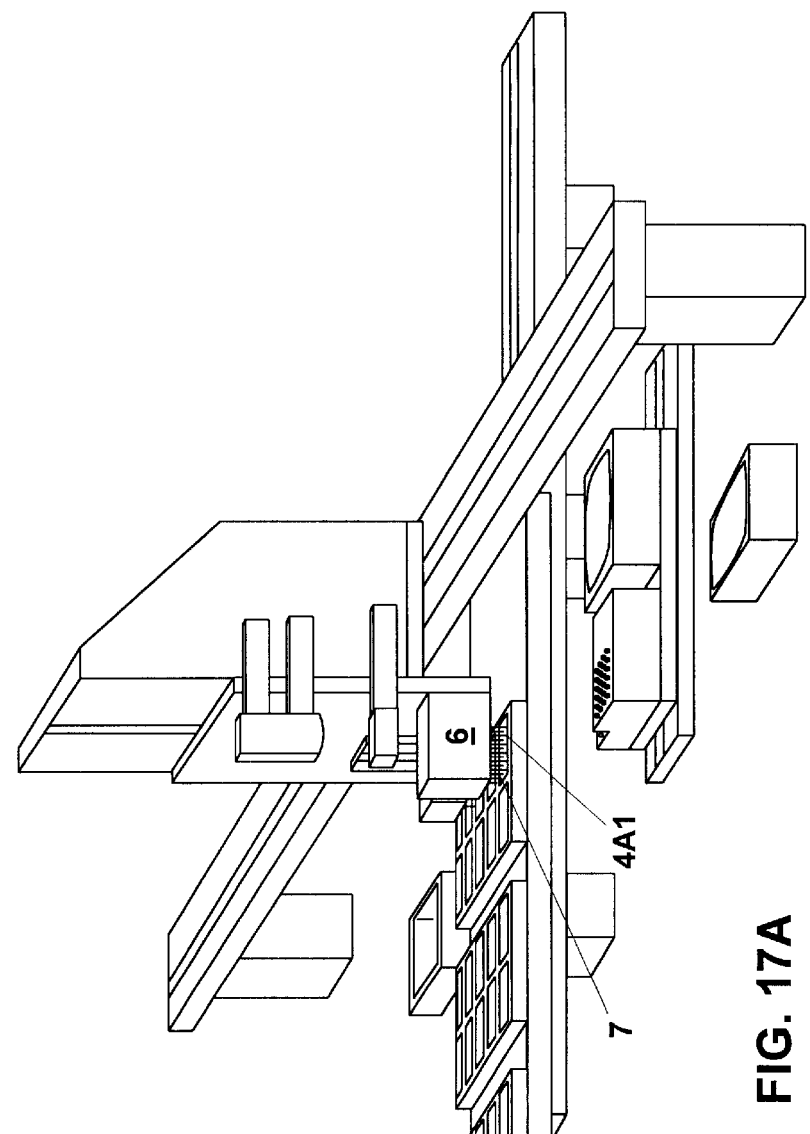
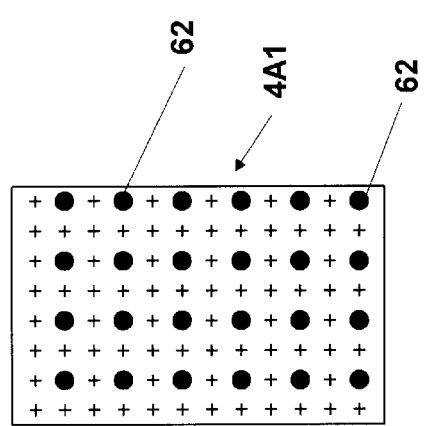
FIG. 17A
FIG. 17B

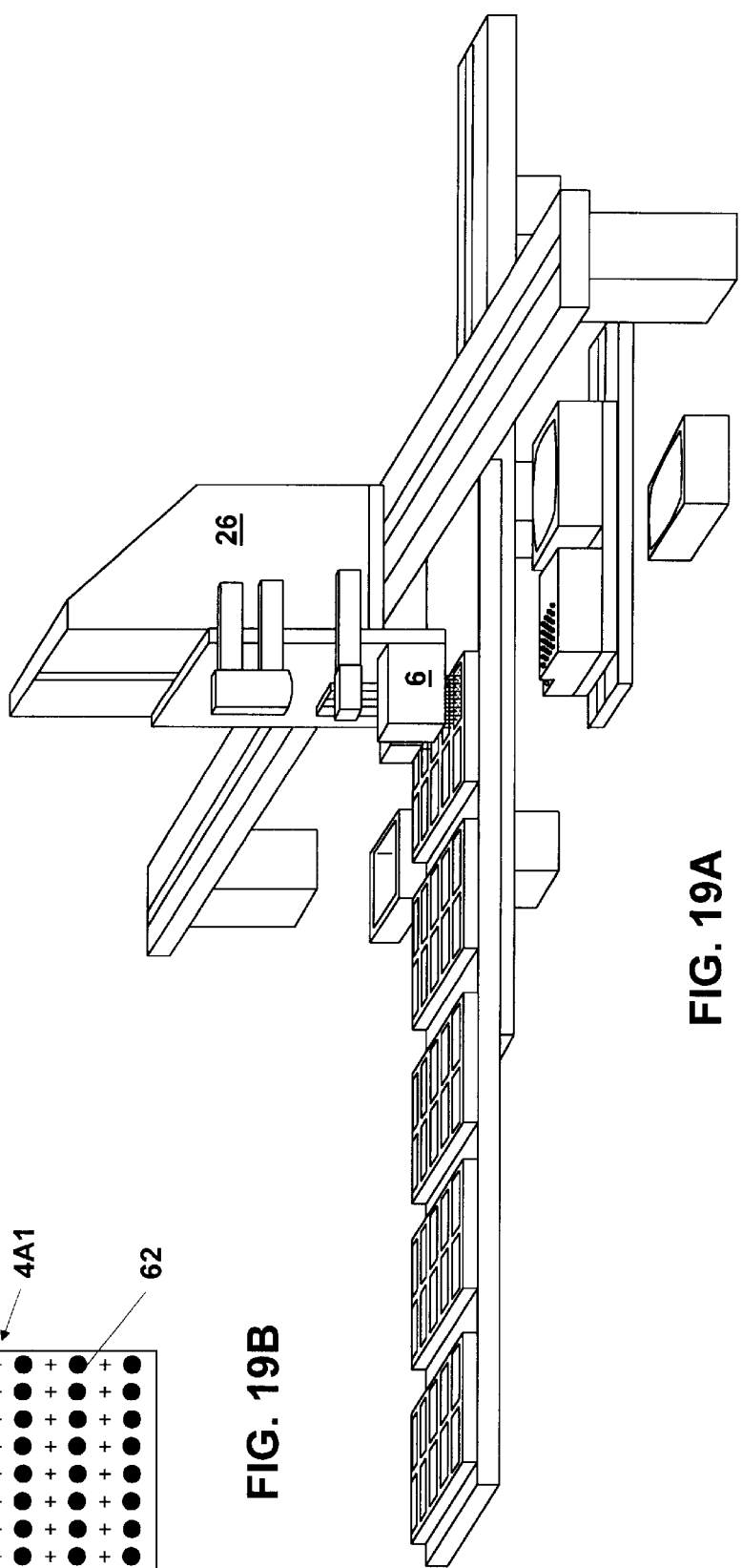
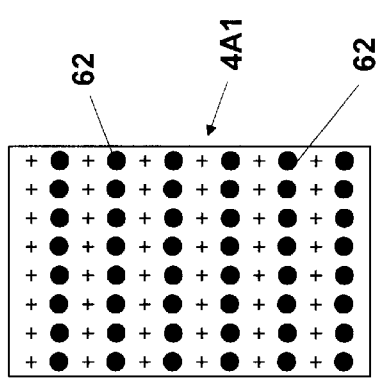
FIG. 19A
FIG. 19B

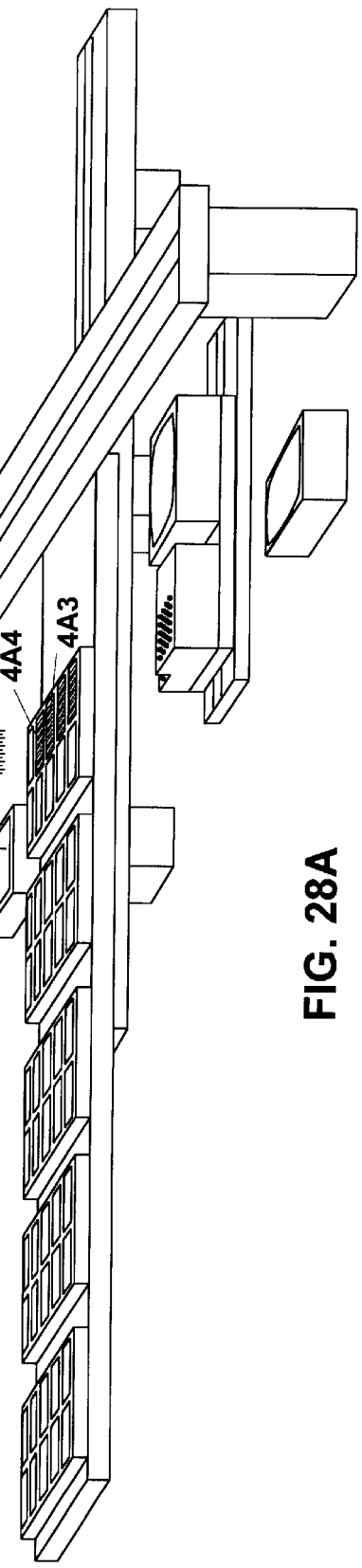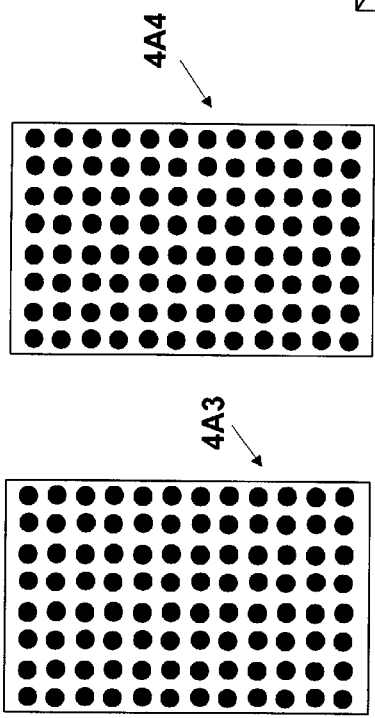
FIG. 28A
FIG. 28B
FIG. 28C

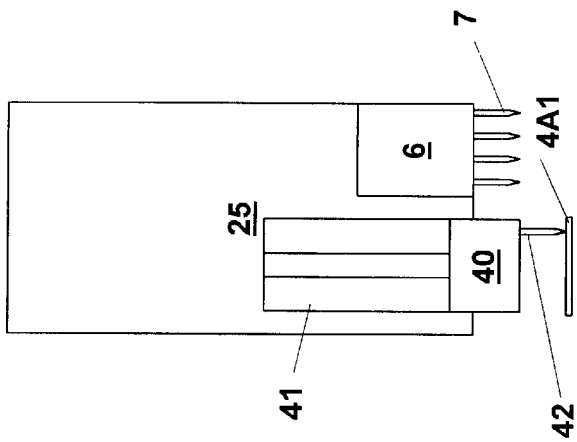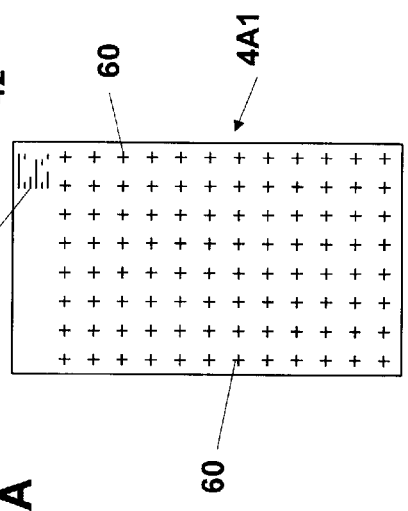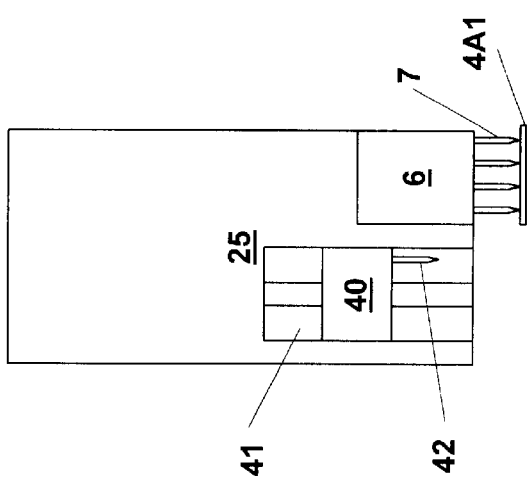

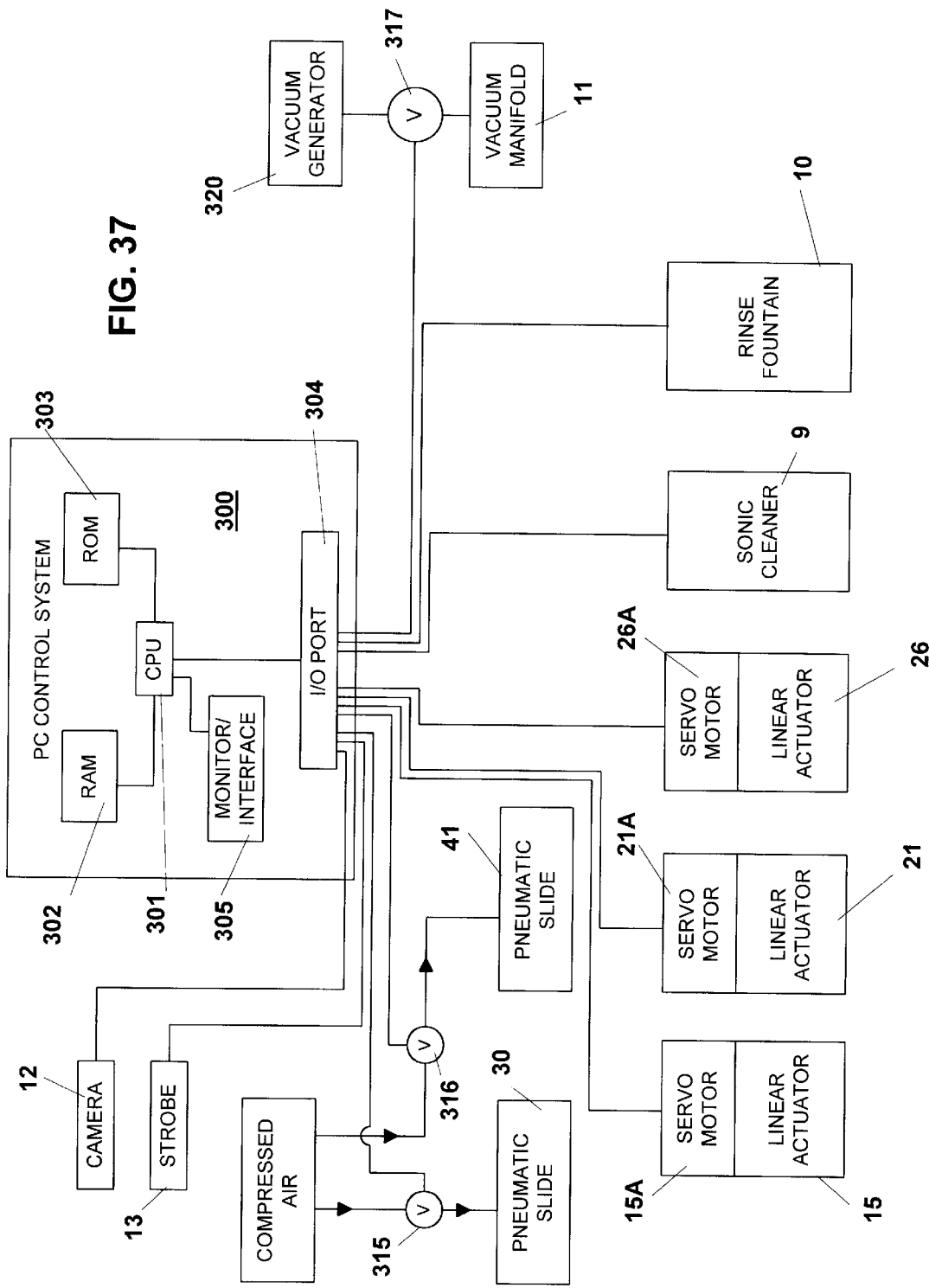

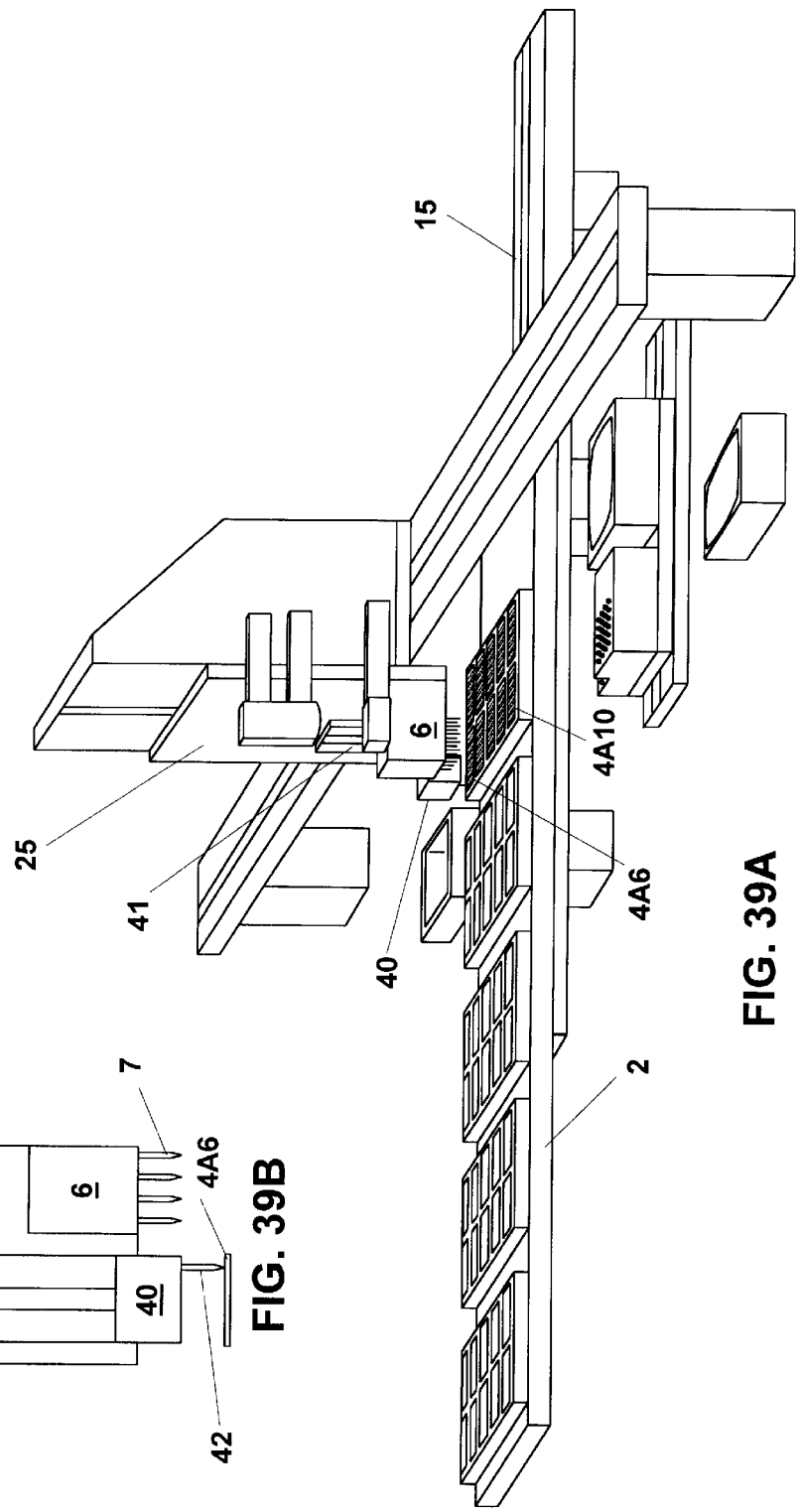

MICROARRAY DISPENSING WITH REAL-TIME VERIFICATION AND INSPECTION

The present invention relates to automated microarray dispensing devices, more specifically it relates to automated microarray dispensing devices with automated quality inspection capability.

BACKGROUND OF THE INVENTION

Microarrays, also known as biochips, have recently become important in the study of genomics. The use of a microarray involves laying down an ordered array of genetic elements onto a solid substrate such as a slide. Depending on the application, a microarray may consist of genomic DNA, reverse-transcribed cDNA, or smaller chains of oligonucleotides as well as any preparatory substrates. The microarray is useful because it allows genetic analysis to take place on a massively parallel scale, wherein thousands of genes and markers can be scored in one experiment.

A microarrayer, also known as a DNA array printer, is a high-capacity system used to print a microarray onto slides. Typically, a microarrayer is a specially built robotic platform designed to transfer solutions from the well of some type of microplate onto another surface for analysis. This process of depositing the liquid spot onto the slide is known as "spotting".

Recently, microarrayers have become extremely popular in laboratories because they add to the efficient productivity of the laboratory to be able to print samples onto slides accurately and rapidly. Affymetrix, Inc., with offices in Santa Clara, Calif., makes an automated arrayer called the 417 ARRAYER (Part No. 0-0001 and Part No. 0-0009). BioRobotics, with offices in Boston, Mass., produces two versions of an automated arrayer called the MICROGRID and MICROGRID II. GeneMachines, with offices in Menlo Park, Calif., makes an arrayer called the OMNIGRID (Model No. OGR-02). Packard Instrument Company with offices in Meriden, Conn. makes an automated arrayer called the BIOCHIP ARRAYER.

Although there are some differences between each of the above listed microarrayers, they are all similar in that they each spot microarrays in an automated fashion. However, there are significant problems with the prior art devices that detracts from their efficient operation.

A first problem arises due to the fact that as blank slides are cycled through prior art microarrayers, they can become askew or positioned improperly underneath dispensing tips. This problem results in spots being positioned improperly on the slides. A second problem can arise even if the slide is positioned correctly under the dispensing tips. It is possible for the spot to be deposited in the correct position, but be of poor quality and therefore useless as far as experimentation purposes.

Up to now, the only way to deal with these problems was to have a human operator visually monitor and inspect the microarrayer during its operation or inspect the samples after they come off the machine. This solution is an unacceptable waste of human effort. The BIOCHIP ARRAYER made by Packard Instrument Company has attempted to deal with the problem of monitoring the spotting process. However, it has only limited verification functionality with its integrated camera. This means that it verifies whether or not a spot has been dispensed, without any quality inspection to analyze whether that spot was good or bad.

What is needed is a better microarrayer with automated quality inspection capability.

SUMMARY OF THE INVENTION

The present invention provides a microarrayer for spotting solution onto slides in an automated microarray dispensing device. Elements of the present invention include at least one dispense head for spotting the slides, at least one light source capable of illuminating the slides, at least one camera operating in conjunction with the at least one light source. The at least one camera is capable of acquiring and transmitting slide image data to a computer. The computer is programmed to receive the slide image and analyze it. The computer will then generate post analysis data based on the analysis of the slide image data. The post analysis data is available for improving the spotting of the solution onto the slides. In a preferred embodiment, the slide image data includes information relating to slide alignment, information relating to spot quality, and slide identification information. In a preferred embodiment, the analysis of the information relating to slide alignment enables the computer to make automatic adjustments to the relative positions of the at least one dispense head and the slides to increase the accuracy of the spotting. In a preferred embodiment, the analysis of the information relating to spot quality identifies a spot as pass or fail. An operator is then able to rework the spot. In a preferred embodiment, the analysis of the slide identification information enables the computer to track each slide.

BRIEF DESCRIPTION OF THE DRAWINGS

FIGS. 3–32 illustrate the sequence of operation of a preferred embodiment of the present invention.

FIG. 34A shows the rework dispense head in the up position.

FIG. 34B shows the rework dispense head in the down position.

FIG. 34C shows a slide with a 2D bar code.

FIG. 37 shows the major components of a preferred embodiment of the present invention.

FIGS. 39A and 39B show the reworking of a slide for a preferred embodiment of the present invention.

DETAILED DESCRIPTION OF THE PREFERRED EMBODIMENT

Figure 1:
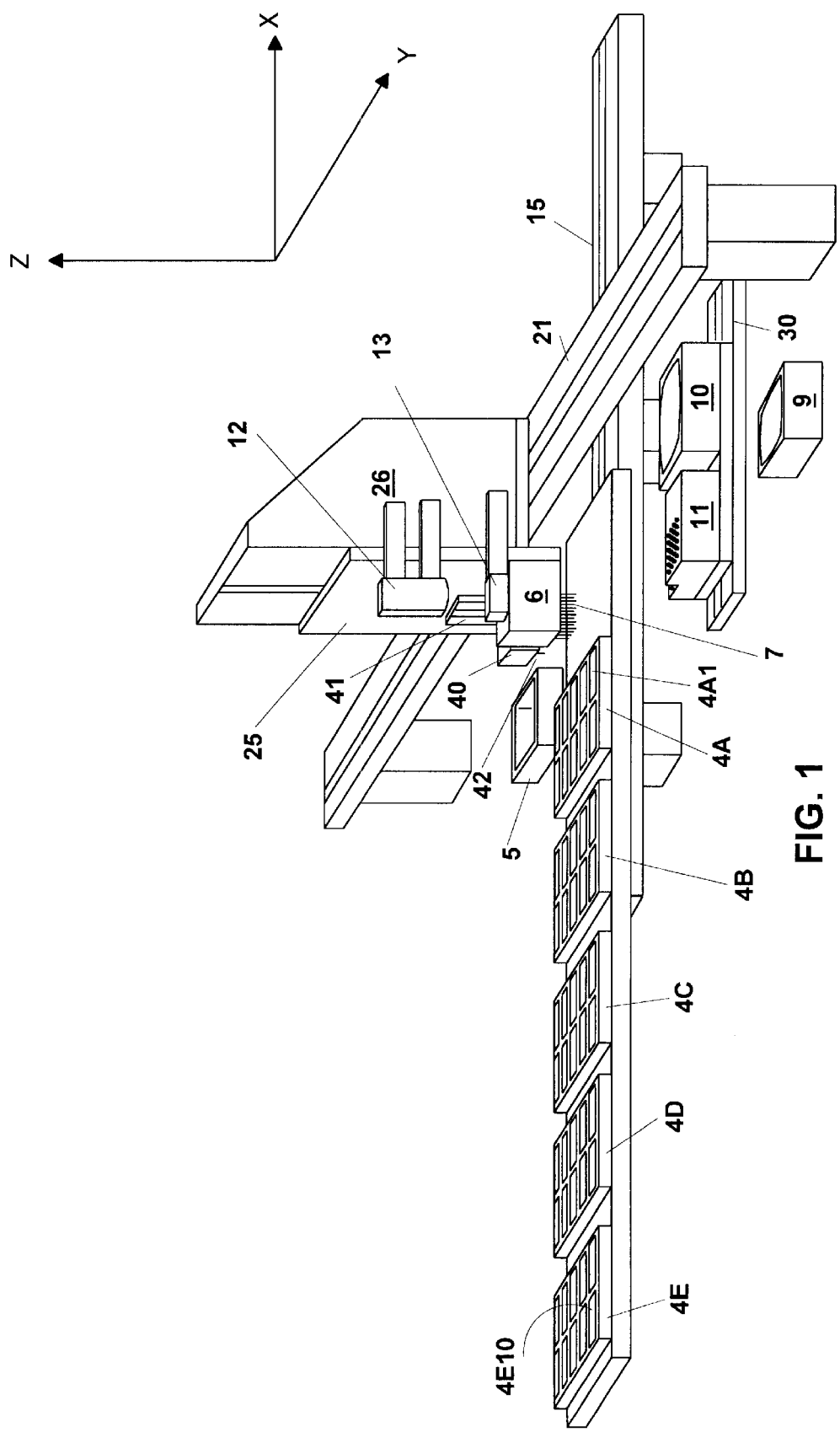
FIG. 1 shows the major components of a preferred embodiment of the present invention.

A detailed description of a preferred embodiment of the present invention can be described by reference to FIGS. 1–38B. During the operation of the present invention, solution from reservoir plate 5 is automatically deposited onto an array of fifty blank slides 4A1–4E10 located on locating plates 4A–4E (see FIG. 1). An operator is able to select via a computer interface whether dispense tip 42 (located underneath dispense head 40) or a 4×6 array of dispense tips 7 (located underneath dispense head 6) will be used to make the deposits onto slides 4A1–4E10. In the preferred embodiment, dispense tips 7 and 42 are quill type dispense tips. Locating plates 4A–4E are mounted on linear actuator 15 so that they can move along the x-axis. Linear actuator 26 is mounted on linear actuator 21 so that linear actuator 26 can move along the y-axis. Dispense heads 6 and 40 are mounted on linear actuator 26 so that they can move along the z-axis. Camera 12 with strobe light 13 is focused so as to permit recording of the deposition process and functions to permit verification of slide identification information and to permit verification of proper deposition of solution on the slides. Periodically, during the cycle, the dispense tips are cleaned in sonic cleaner 9, rinsed in rinse fountain 10, and then dried in vacuum manifold 11. After the solution has been deposited onto the slides, the operator can retrieve locating plates 4A–4E containing slides 4A1–4E10 from the position shown in FIG. 2.

Sequence of Operation of a Preferred Embodiment

FIGS. 3–32 illustrate the sequence of operation of a preferred embodiment of the present invention.

In a preferred embodiment of the present invention, the operation of the components is controlled by PC control system 300, as shown in FIG. 37. FIGS. 38A–38E show a flowchart representing preferred programming of PC. control system 300 and corresponds to the sequence illustrated in FIGS. 3–32.

Figure 3:
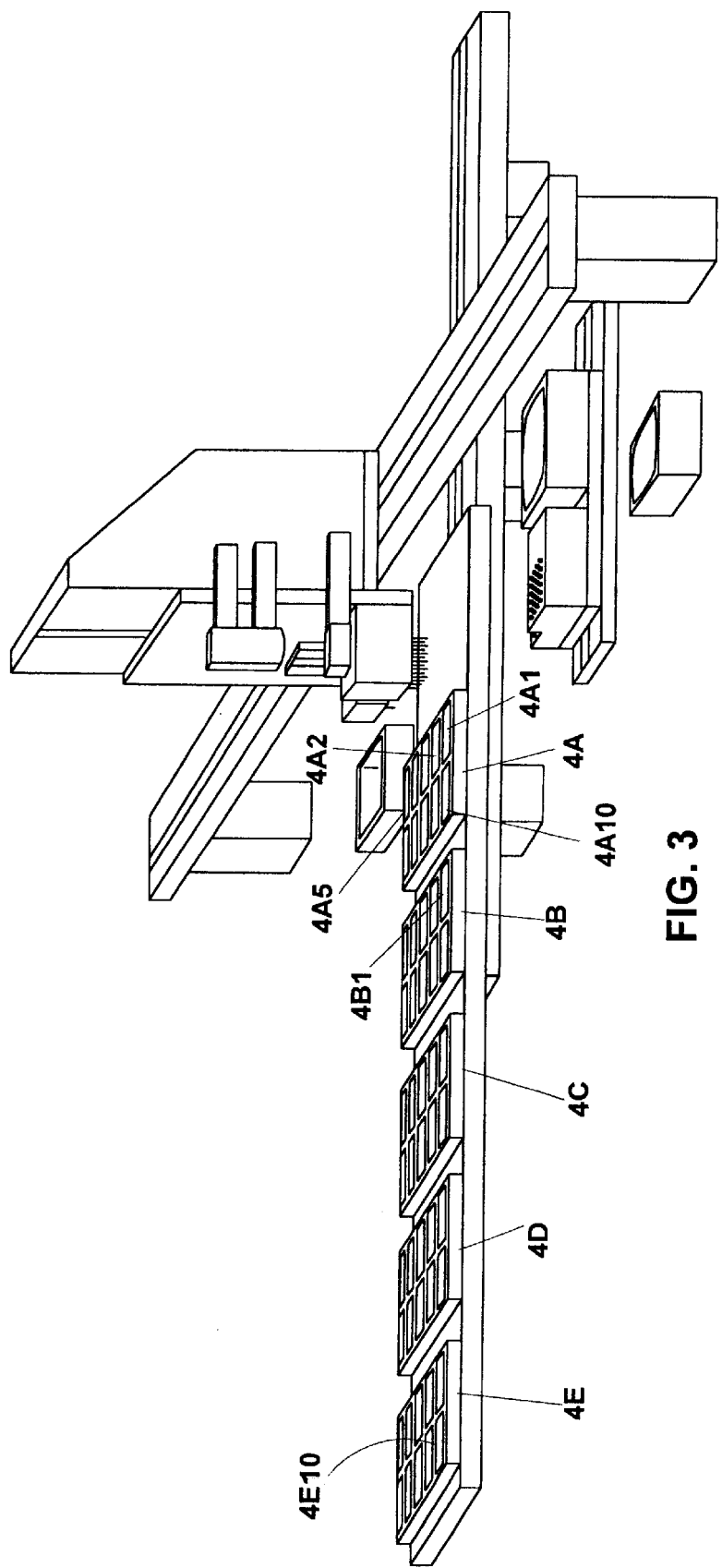
Figure 16B:
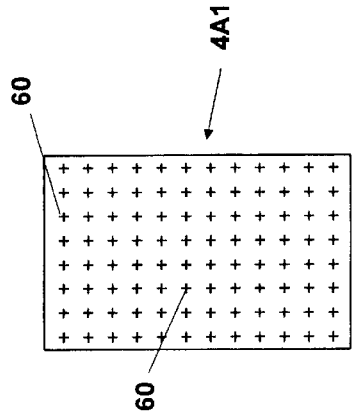

As shown in FIG. 3, an operator places five locating plates 4A–4E each having ten clean, blank slides 4A1–4E10 on platform 2. In a preferred embodiment of the present invention, slides 4A1–4E10 are made by Sequonem with offices in San Diego, Calif. A preferred slide is shown in FIG. 16B. It has ninety-six etched dispense positions 60 and has its own unique 2D bar code 65 for identification purposes.

Figure 4:
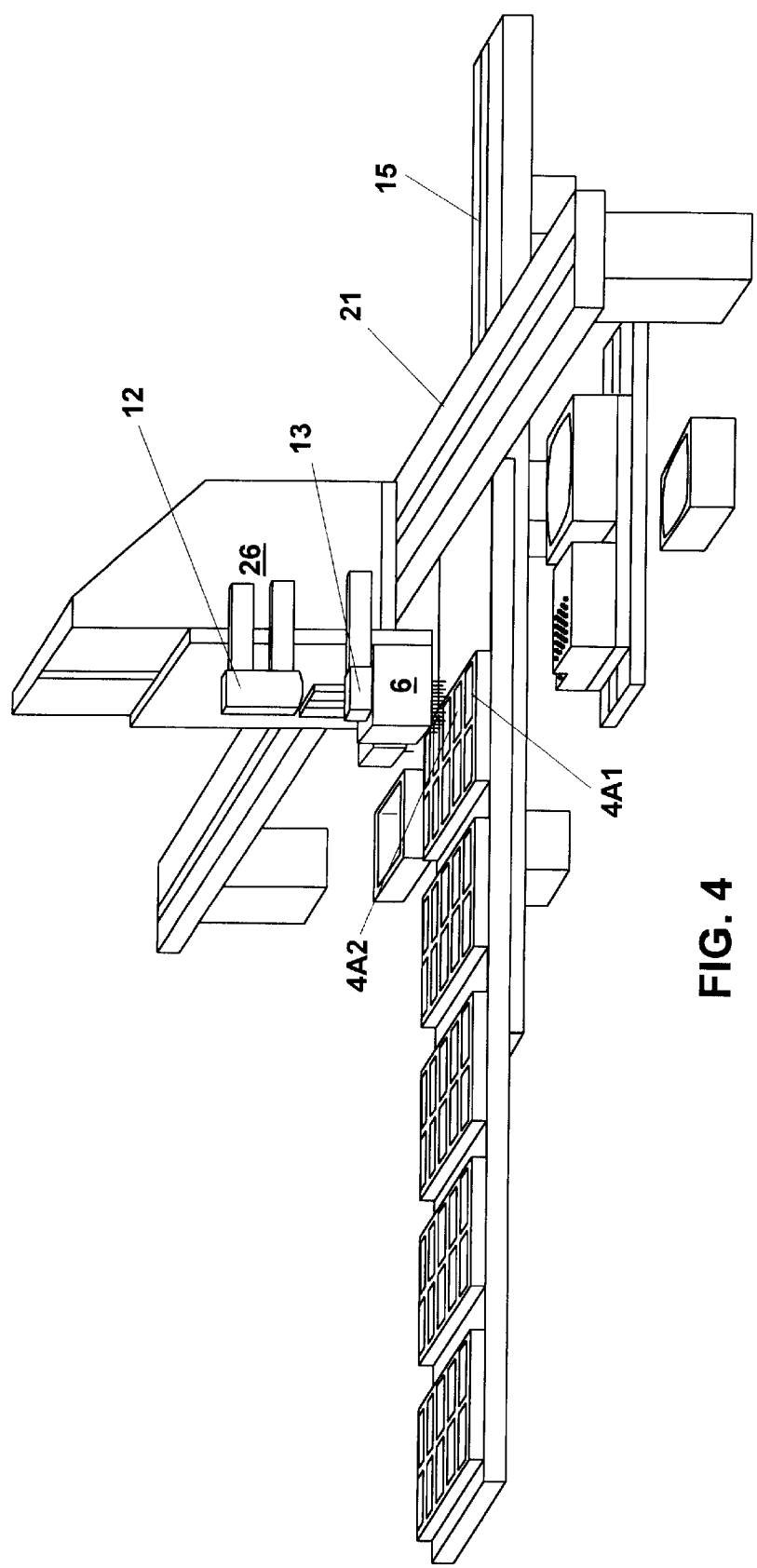

As shown in FIG. 4, linear actuator 15 moves platform 2 so that slide 4A1 is underneath the dispense head 6. Dispense head 6 is positioned directly above slide 4A1. Using camera 12 and the strobe light 13, an image is acquired of slide 4A1. The camera reads the bar code and inspects the positioning and alignment of slide 4A1 on locating plate 3A. The software then analyzes the position data and stores the information. The information stored and will be used later to adjust the positions of slide 4A1 and dispense head 6 to ensure accurate placement of the solution on the slide.

Figure 5:
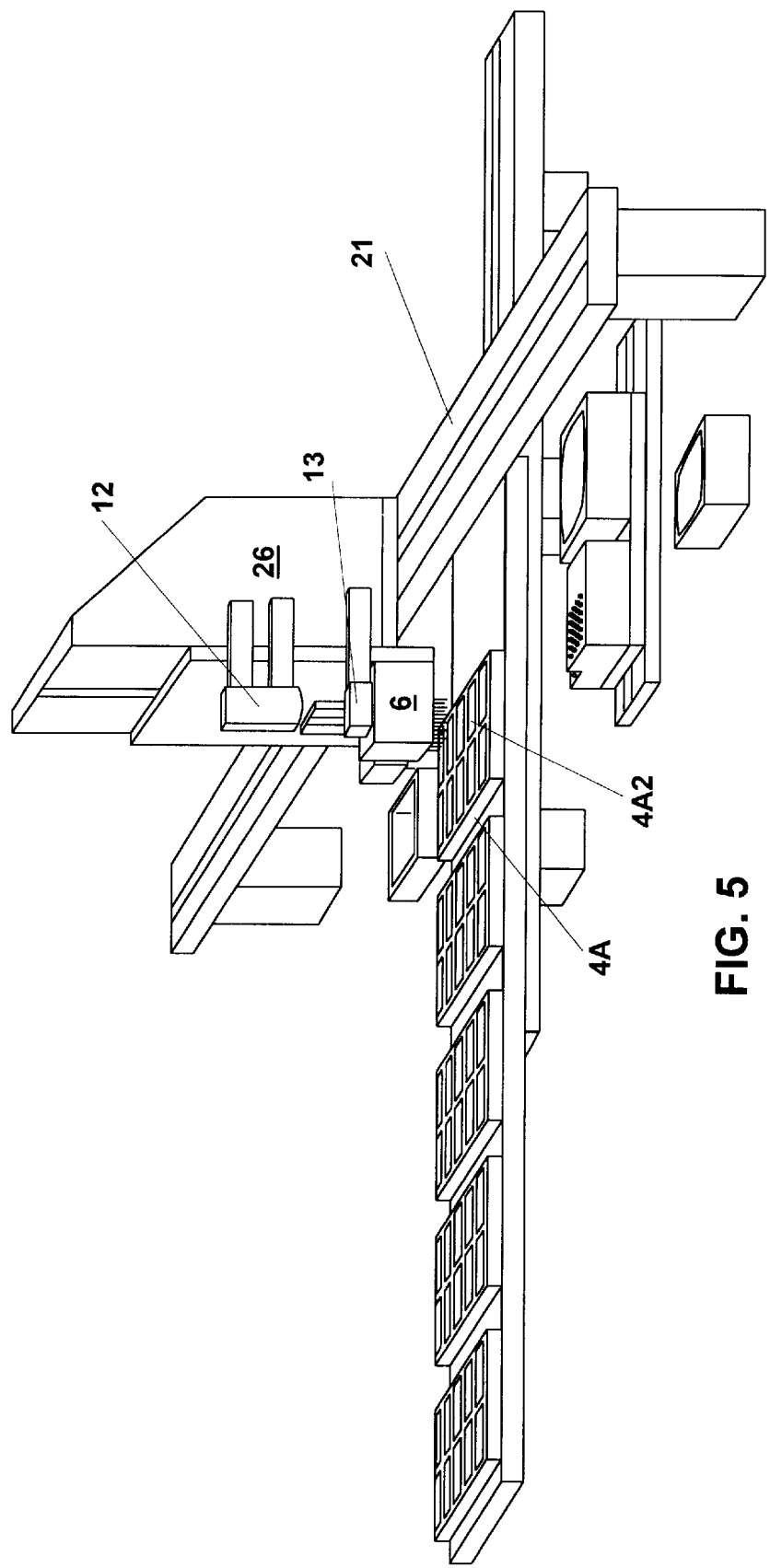

After camera 12 has acquired the image of slide 4A1, linear actuator 26 is moved via linear actuator 21 to the position shown in FIG. 5 so that dispense head 6 is directly above slide 4A2. Using camera 12 and the strobe light 13, an image is acquired of slide 4A2. As with slide 4A1, camera reads the bar code and inspects the positioning and alignment of slide 4A2 on locating plate 4A. The software then analyzes the position data and stores the information. The information stored and will be used later to adjust the positions of slide 4A2 and dispense head 6 to ensure accurate placement of the solution on the slide.

Figure 6:
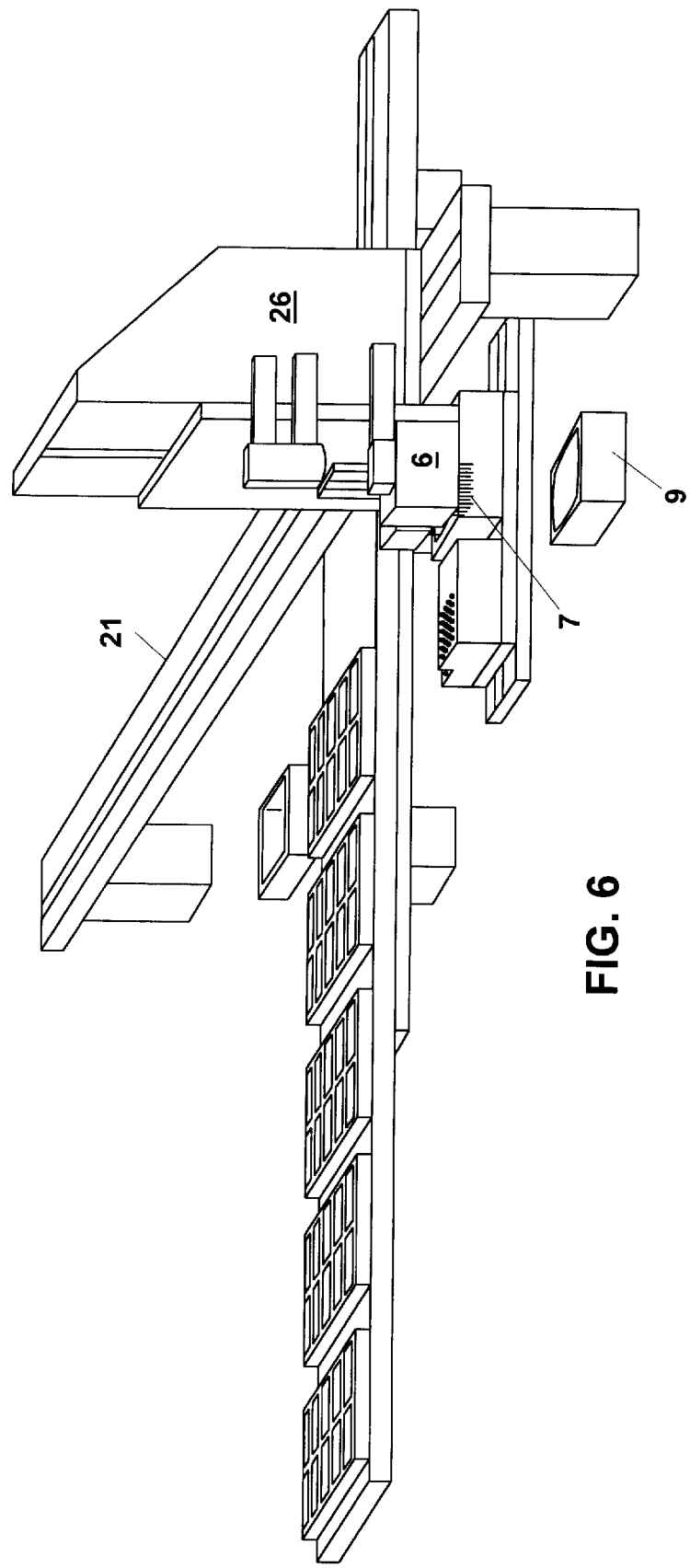

Linear actuator 26 is then moved via linear actuator 21 to the position shown in FIG. 6 so that dispense head 6 is directly above sonic cleaner 9.

Figure 7:
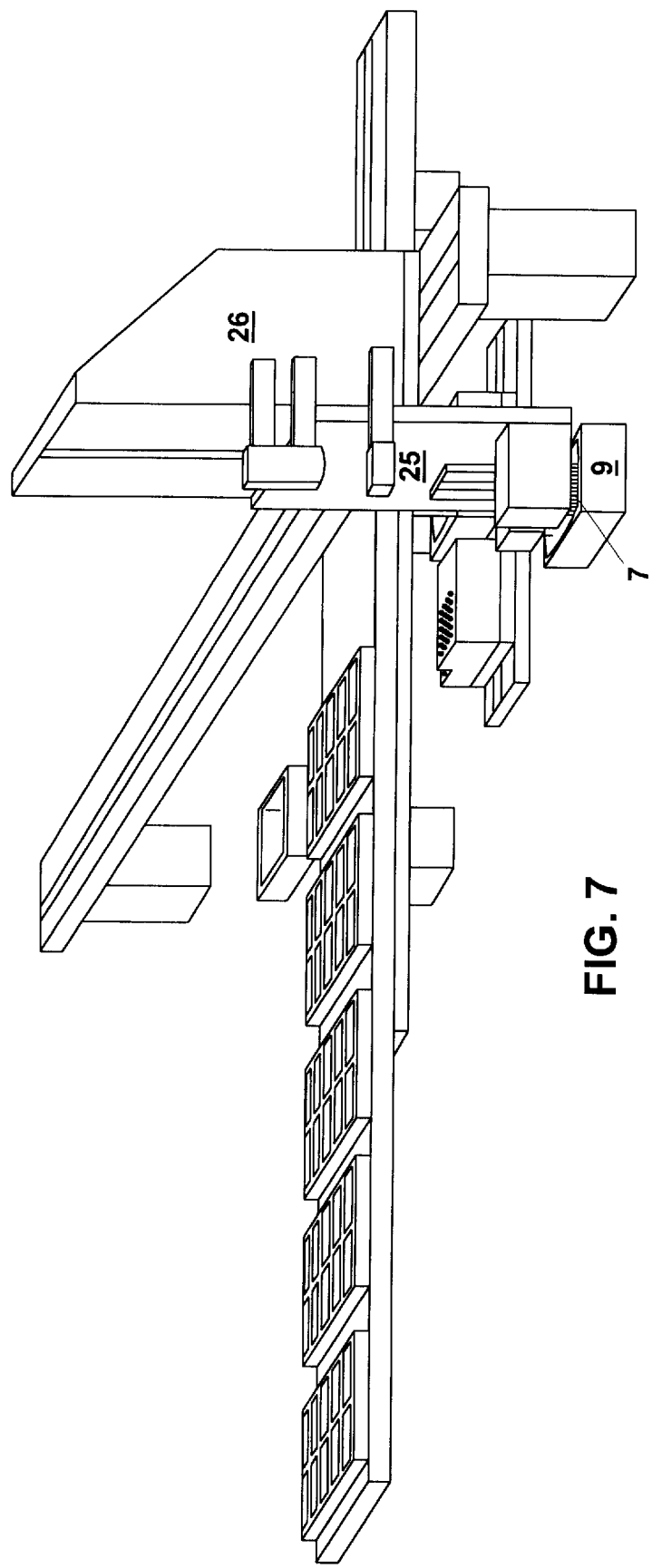
Figure 8:
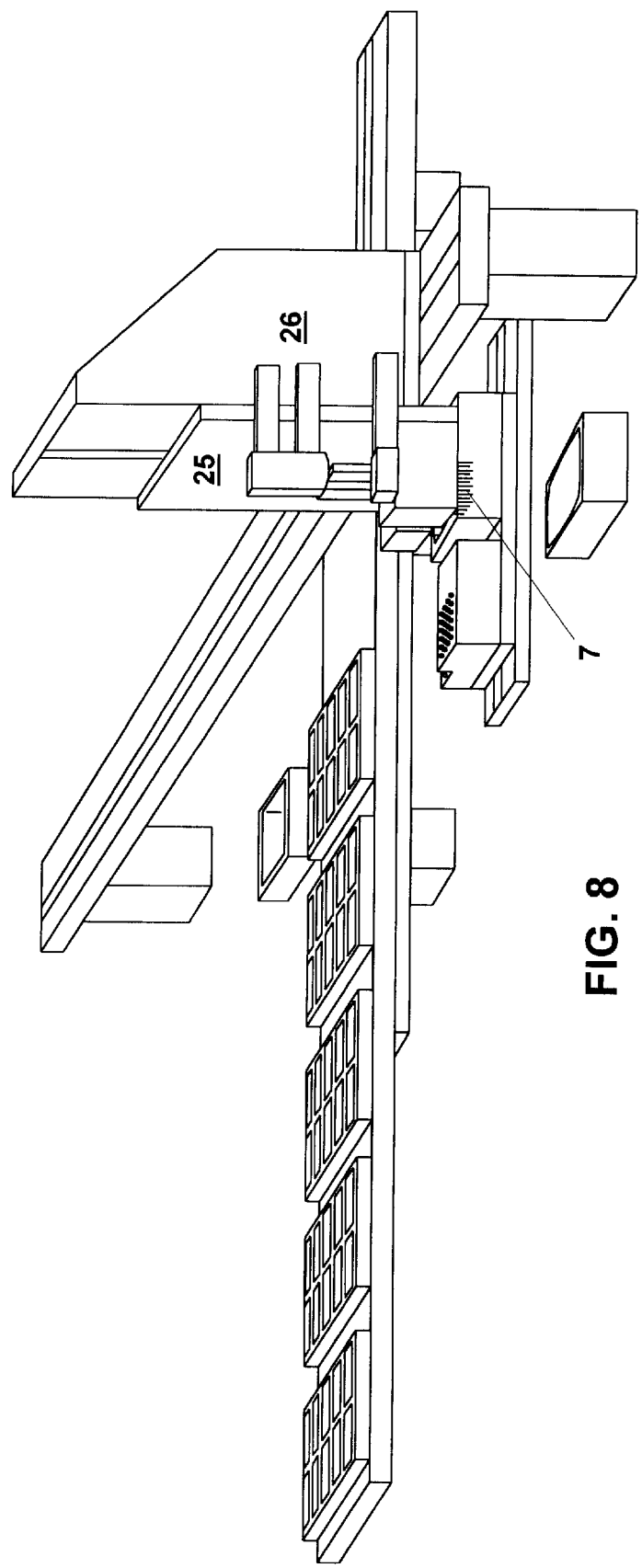

As shown in FIG. 7, mounting plate 25 moves downward via linear actuator 26 so that dispense tips 7 are dipped in sonic cleaner 9 for a programmable time period while the cleaner is turned on. When finished, mounting plate 25 moves upward as shown in FIG. 8.

Figure 9:
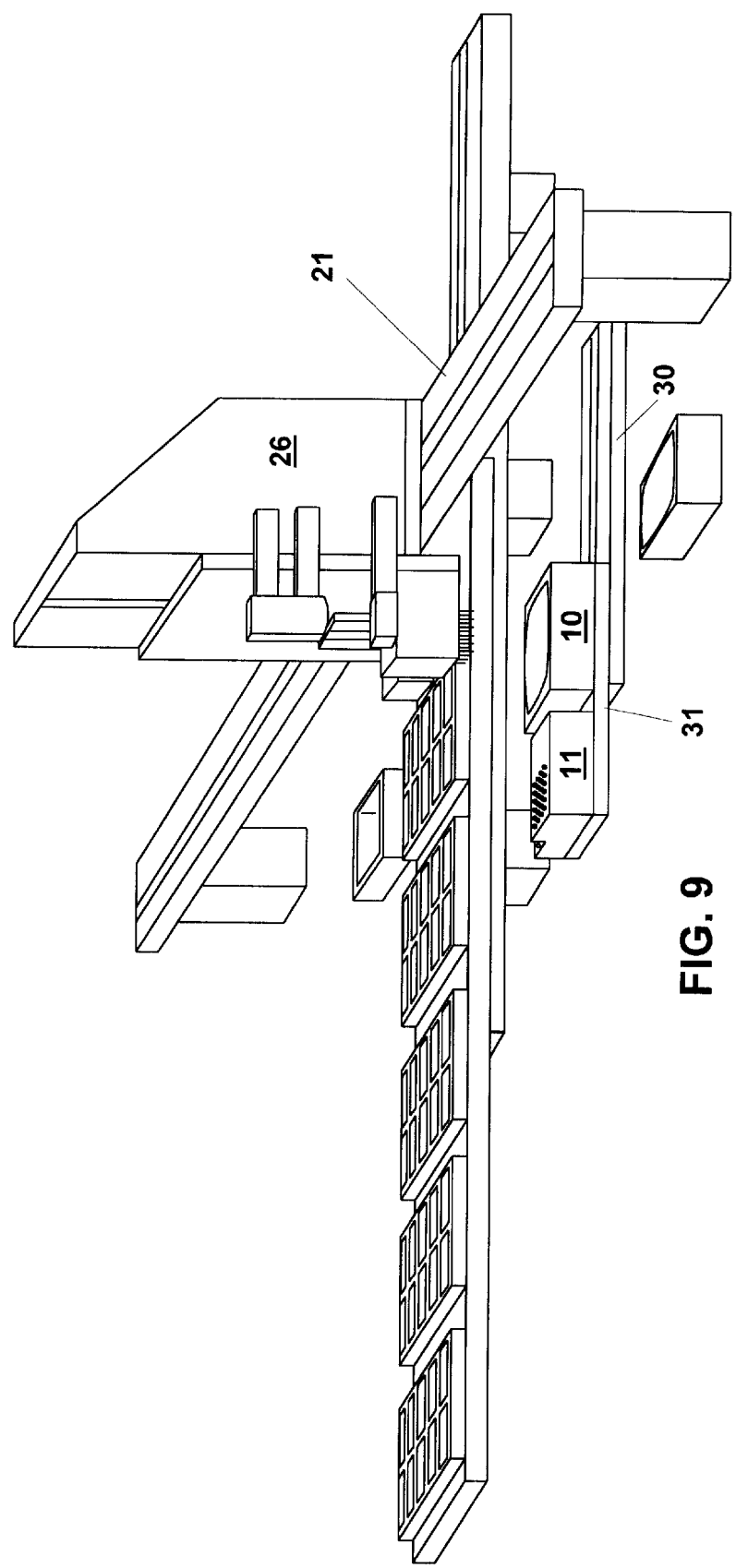

Then, as shown in FIG. 9, platform 31 moves to the left via pneumatic slide 30, thereby moving rinse fountain 10 and vacuum manifold 11 to the left. Linear actuator 26 is moved via linear actuator 21 back so that it is directly above rinse fountain 10.

Figure 10:
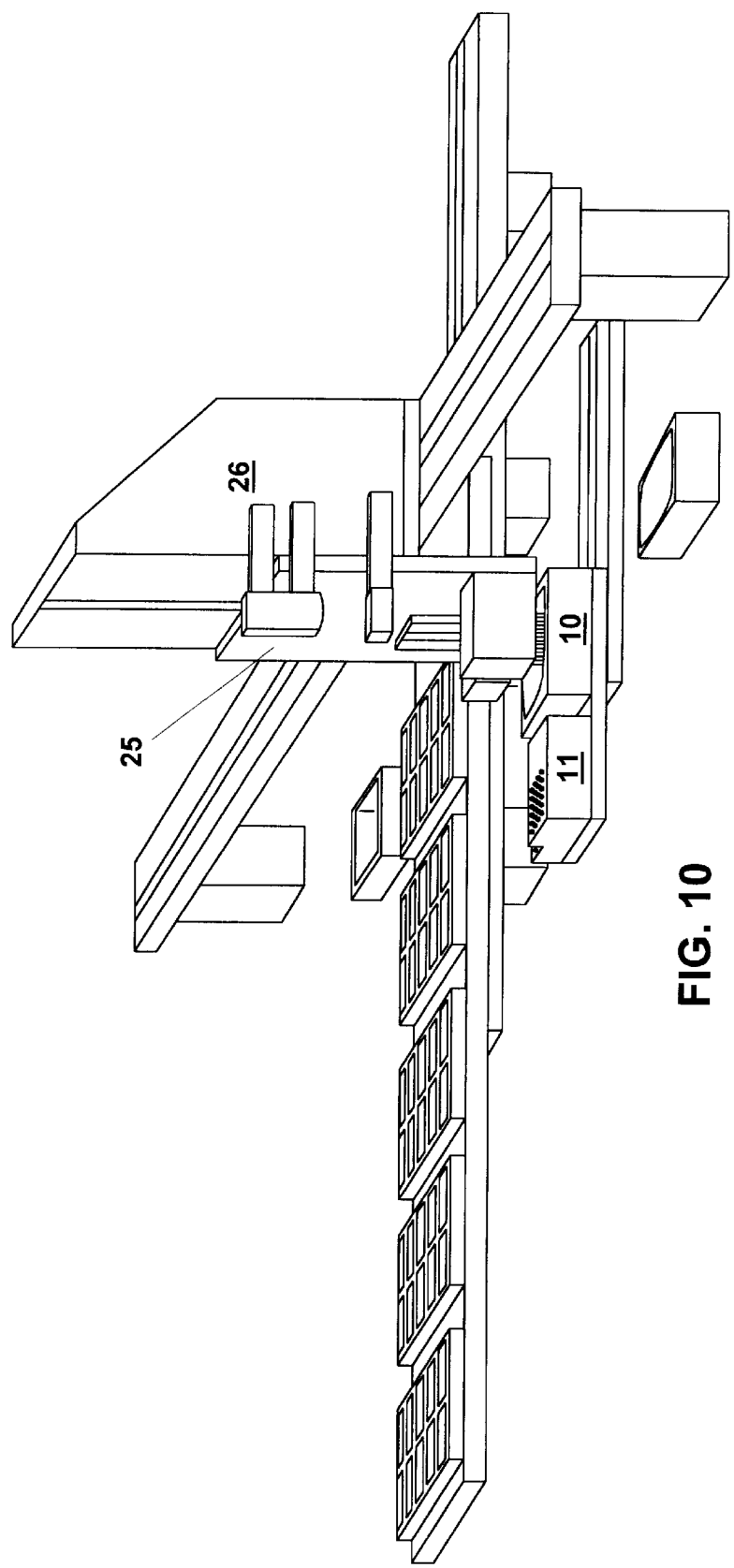

As shown in FIG. 10, mounting plate 25 moves downward via linear actuator 26 so that tips 7 are dipped in rinse fountain 10 for a programmable time period while the fountain is turned on.

Figure 11:
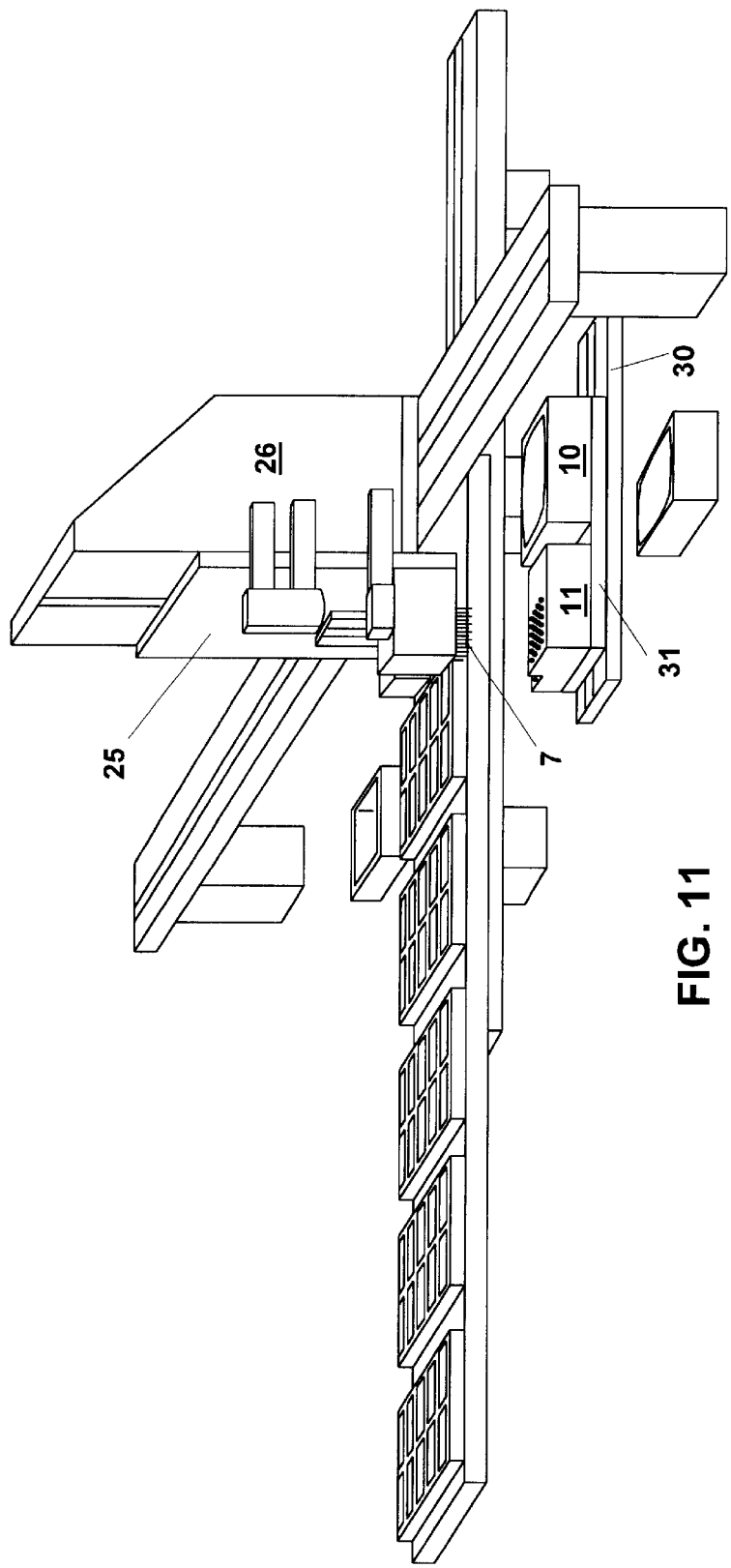

After rinsing, mounting plate 25 moves upward via linear actuator 26, as shown in FIG. 11. Platform 31 moves to the right via pneumatic slide 30, thereby moving rinse fountain 10 and vacuum manifold 11 to the right.

Figure 12:
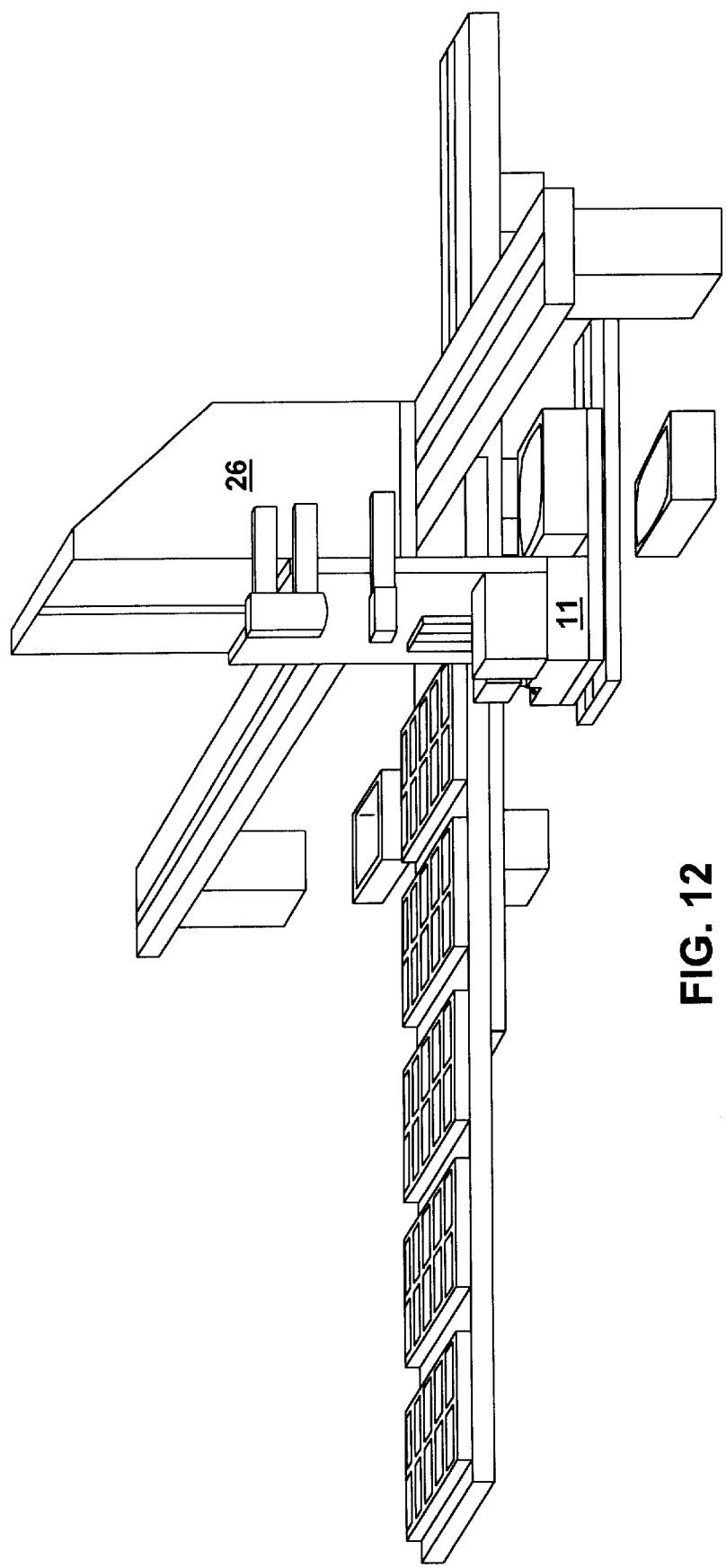

As shown in FIG. 12, dispense tips 7 are then lowered into the vacuum manifold 11 via linear actuator 26 and the vacuum is turned on for a programmable time period, thereby drying dispense tips 7. This cleaning cycle can be set by the user, via the computer interface, to be repeated as many times as necessary.

Figure 13:
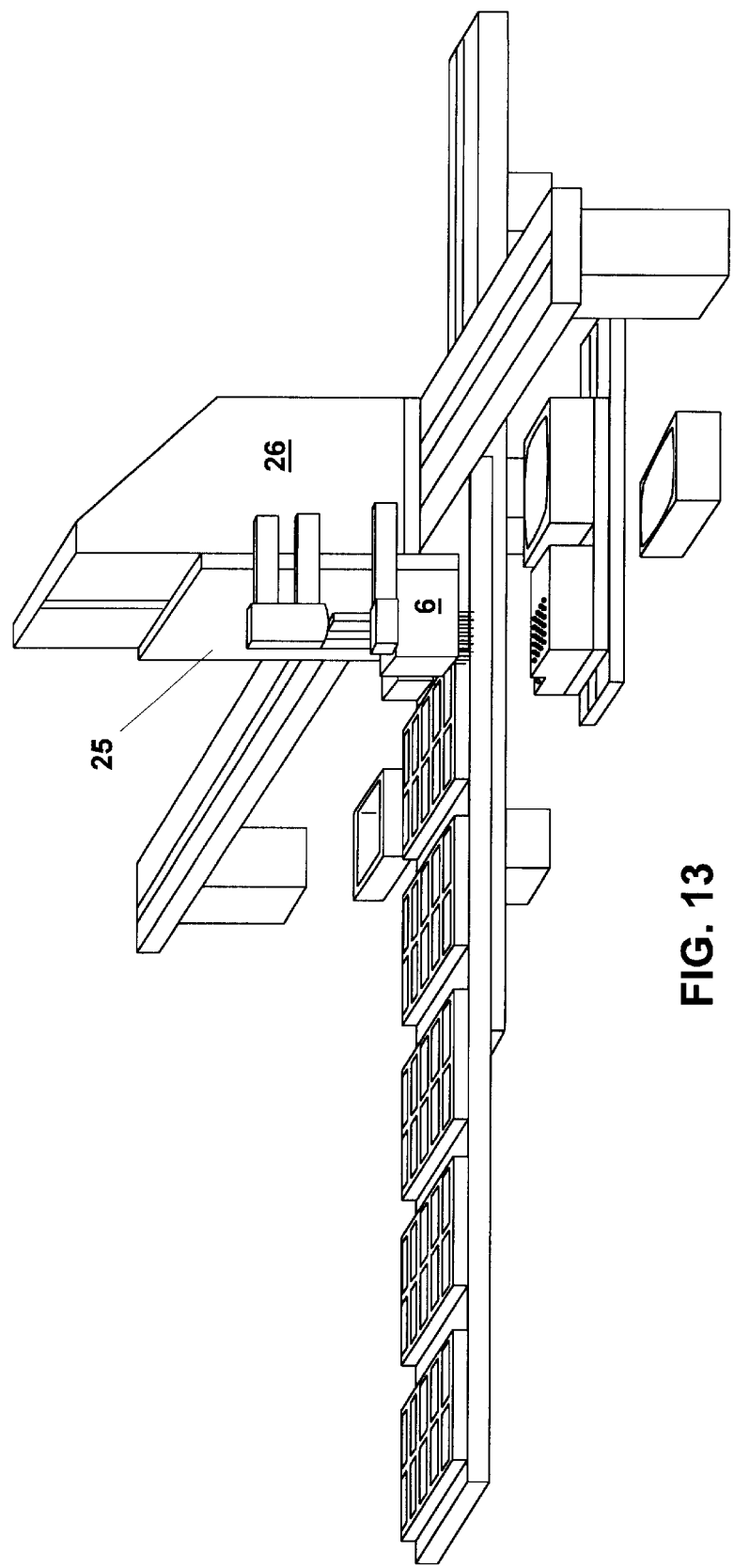
Figure 14:
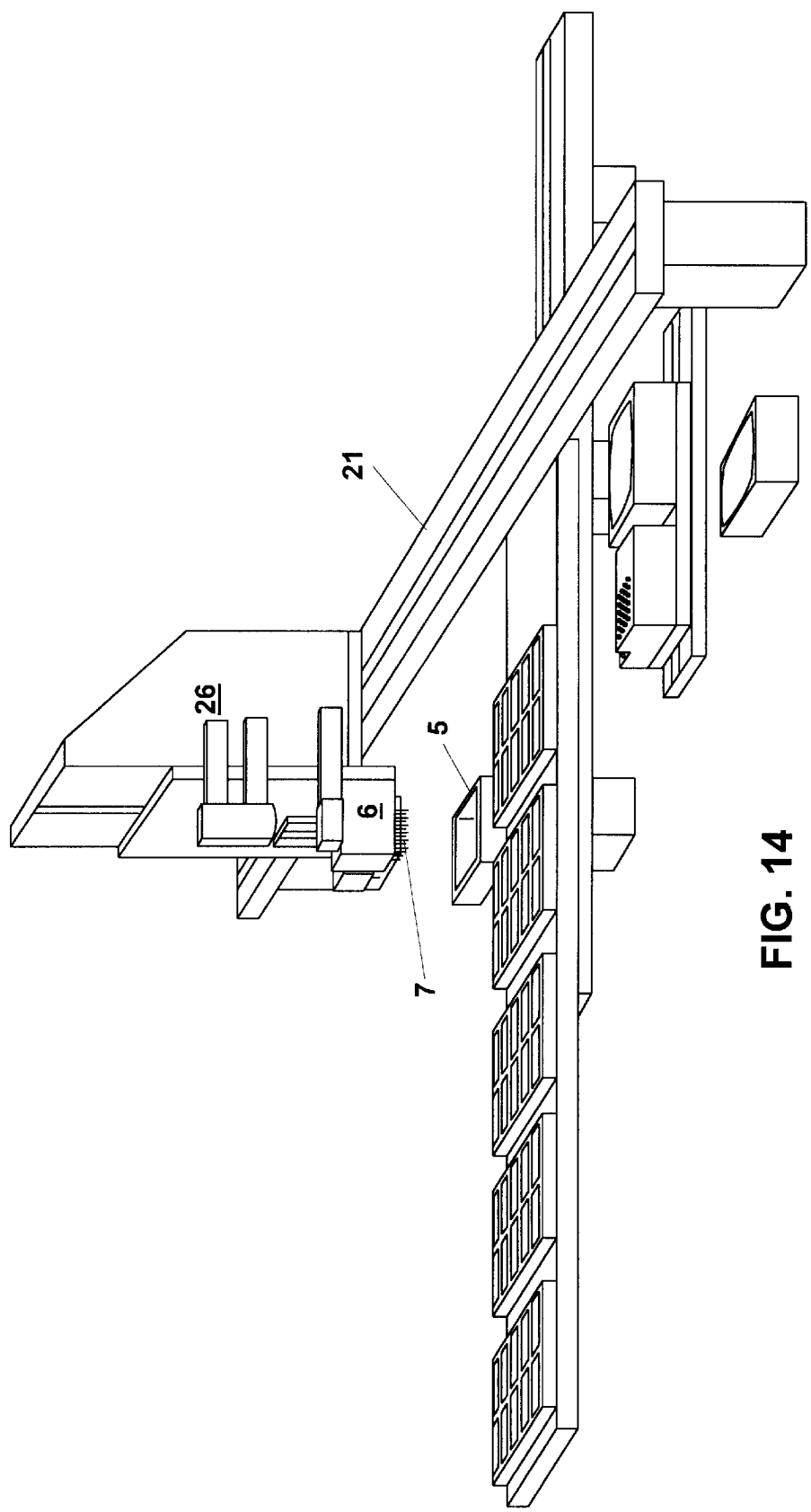

Mounting plate 25 is then raised via linear actuator 26 as shown in FIG. 13. Linear actuator 26 is then moved via linear actuator 21 so that dispense head 6 is directly above reservoir plate 5, as shown in FIG. 14.

Figure 15:
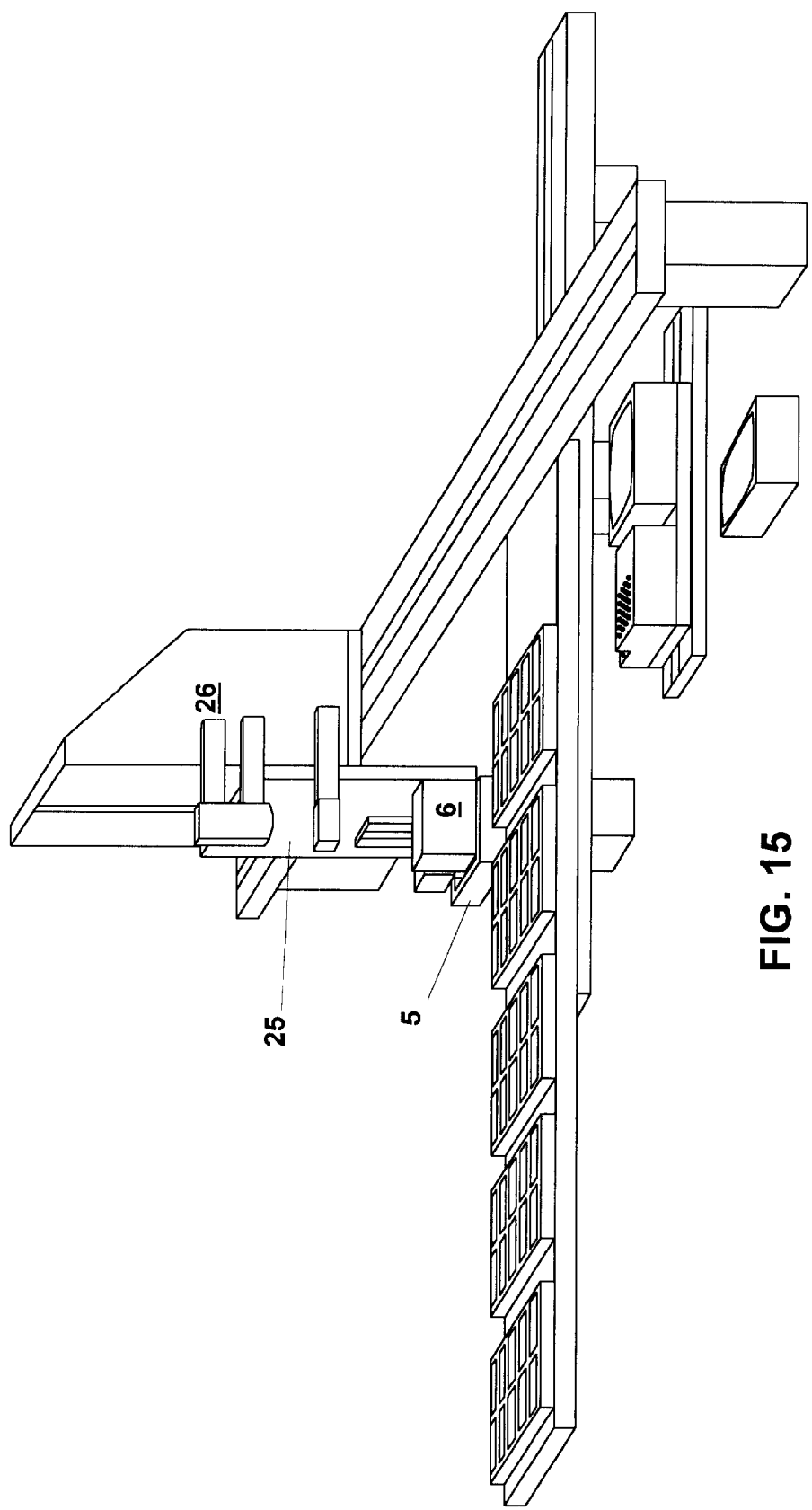

Mounting plate 25 is then lowered via linear actuator 26 so that tips 7 are dipped into the solution contained in reservoir plate 5, as shown in FIG. 15. While in reservoir plate 5, dispense tips 7 pick up some of the solution to be dispensed.

Figure 16A:
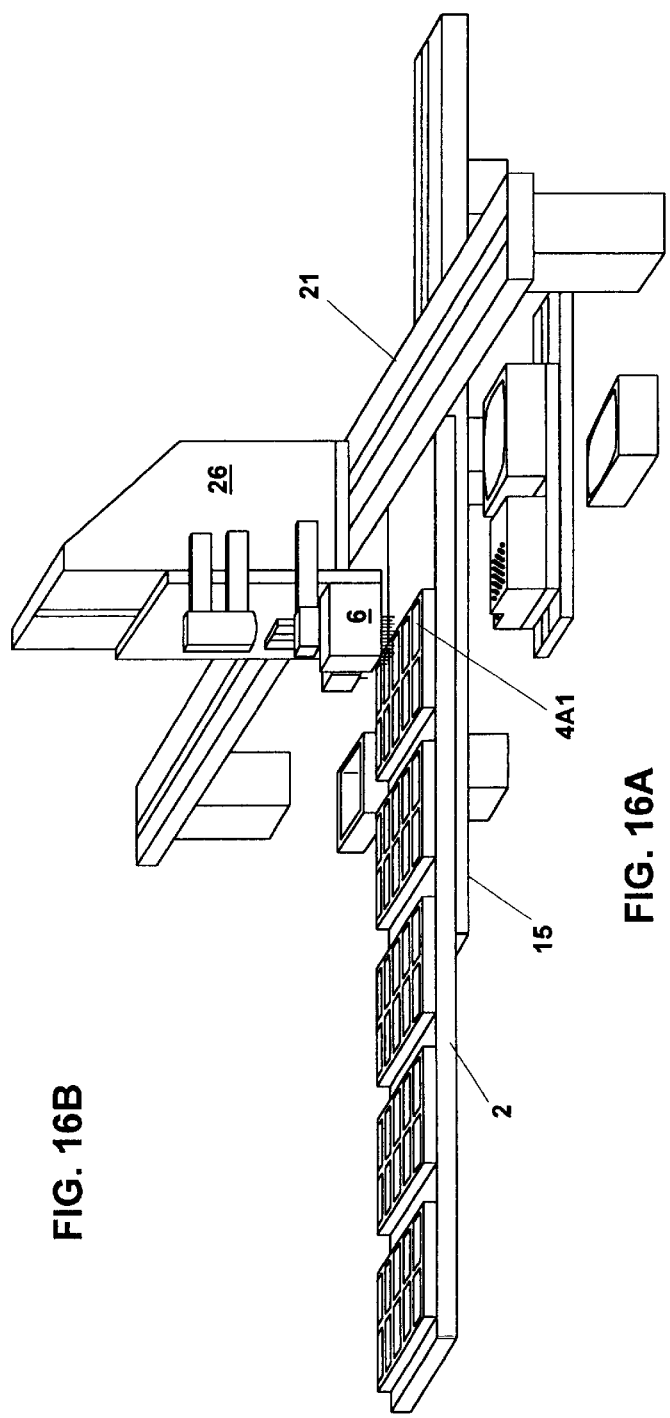

Linear actuator 26 then moves to the first dispense position shown in FIG. 16A so that dispense head 6 is above slide 4A1. Based on the earlier positioning data regarding slide 4A1 (see discussion of FIG. 4), linear actuator 21 makes minute positioning adjustments to linear actuator 26 and linear actuator 15 makes minute positioning adjustments to platform 2 in order to accurately position dispense head 6 over slide 4A1 at the first dispense position.

FIG. 16B shows a top view of a blank slide 4A1. In this preferred embodiment, slide 4A1 has 96 positions 60 arranged in an 8×12 array. At each position 60, slide 4A1 is etched so as to be better able to retain a drop of solution deposited at the spot.

Dispense head 6 is then lowered via linear actuator 26 so that tips 7 are in contact with slide 4A1 at the first dispense position, as shown in FIG. 17A. As tips 7 contact slide 4A1, spots 62 are placed on slide 4A1 via surface tension, as shown in FIG. 17B.

Figure 18:
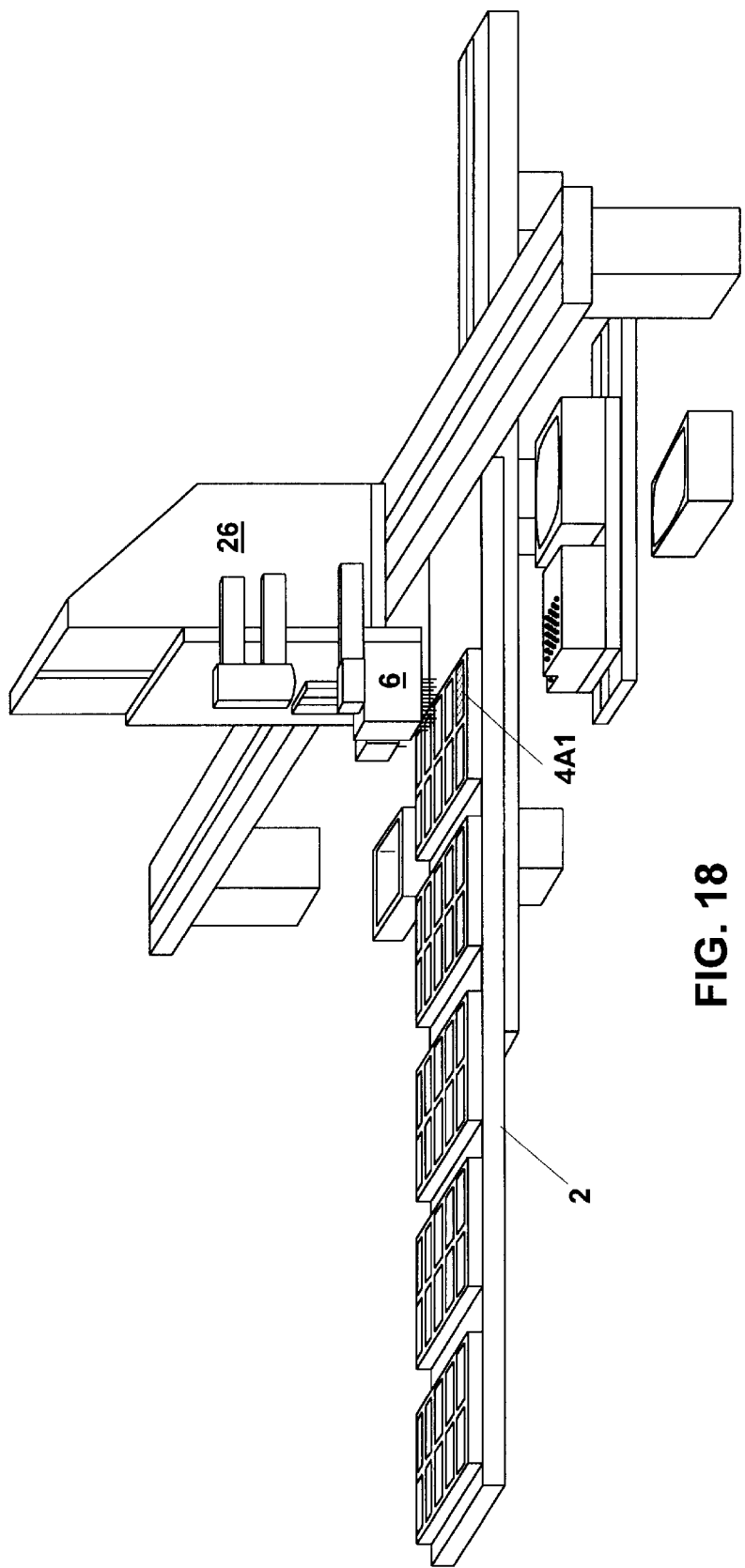

Dispense head 6 is raised via linear actuator 26, as shown in FIG. 18. Based on the earlier positioning data regarding slide 4A1, linear actuator 21 makes minute positioning adjustments to linear actuator 26 and linear actuator 15 makes minute positioning adjustments to platform 2 in order to accurately position dispense head 6 over slide 4A1 at the second dispense position.

Dispense head 6 is then lowered via linear actuator 26 so that tips 7 are in contact with slide 4A1 at the second dispense position, as shown in FIG. 19A. As tips 7 contact slide 4A1, more spots 62 are added to slide 4A1, as shown in FIG. 19B.

Figure 20:
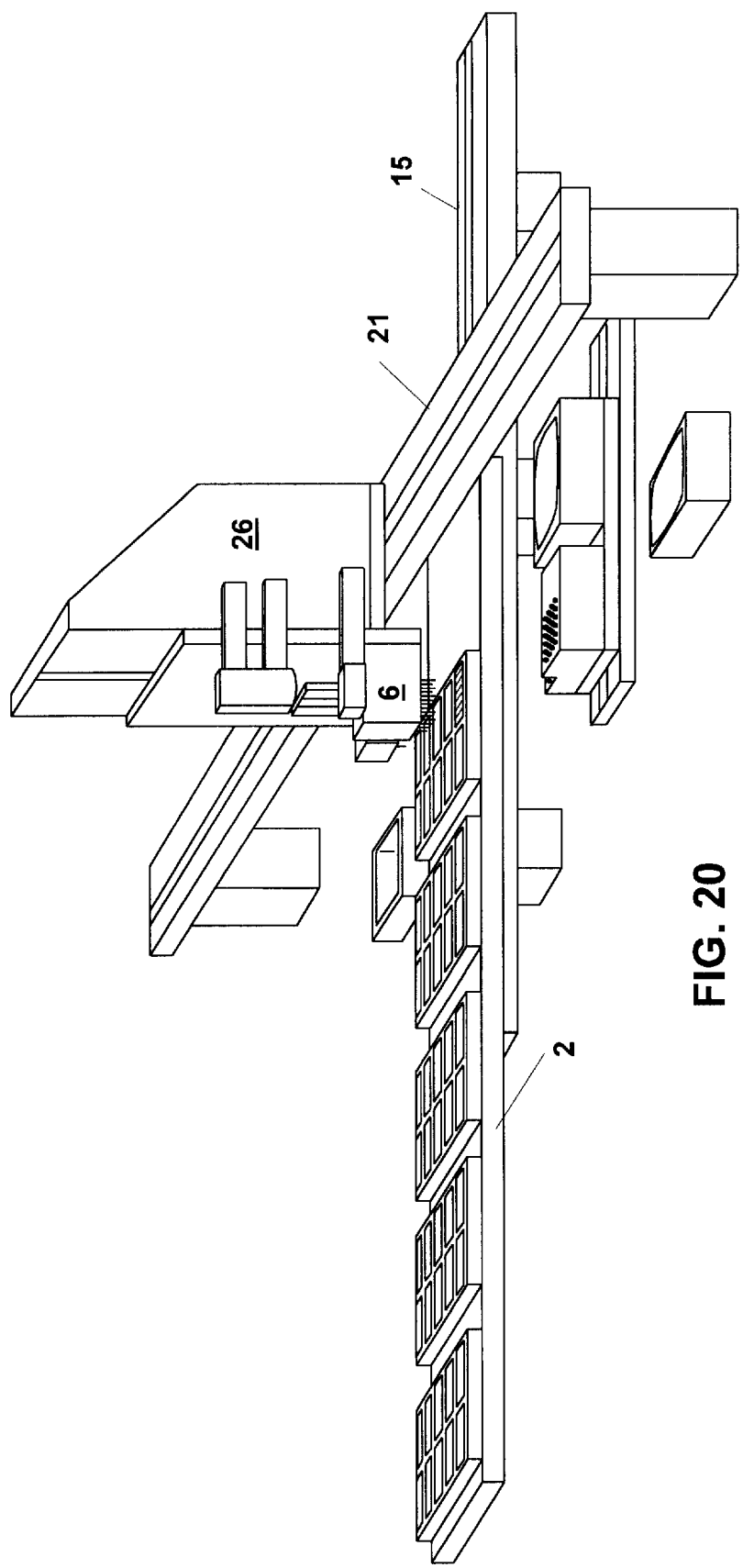

Dispense head 6 is raised via linear actuator 26, as shown in FIG. 20. Based on the earlier positioning data regarding slide 4A1, linear actuator 21 makes minute positioning adjustments to linear actuator 26 and linear actuator 15 makes minute positioning adjustments to platform 2 in order to accurately position dispense head 6 over slide 4A1 at the third dispense position.

Figure 21A:
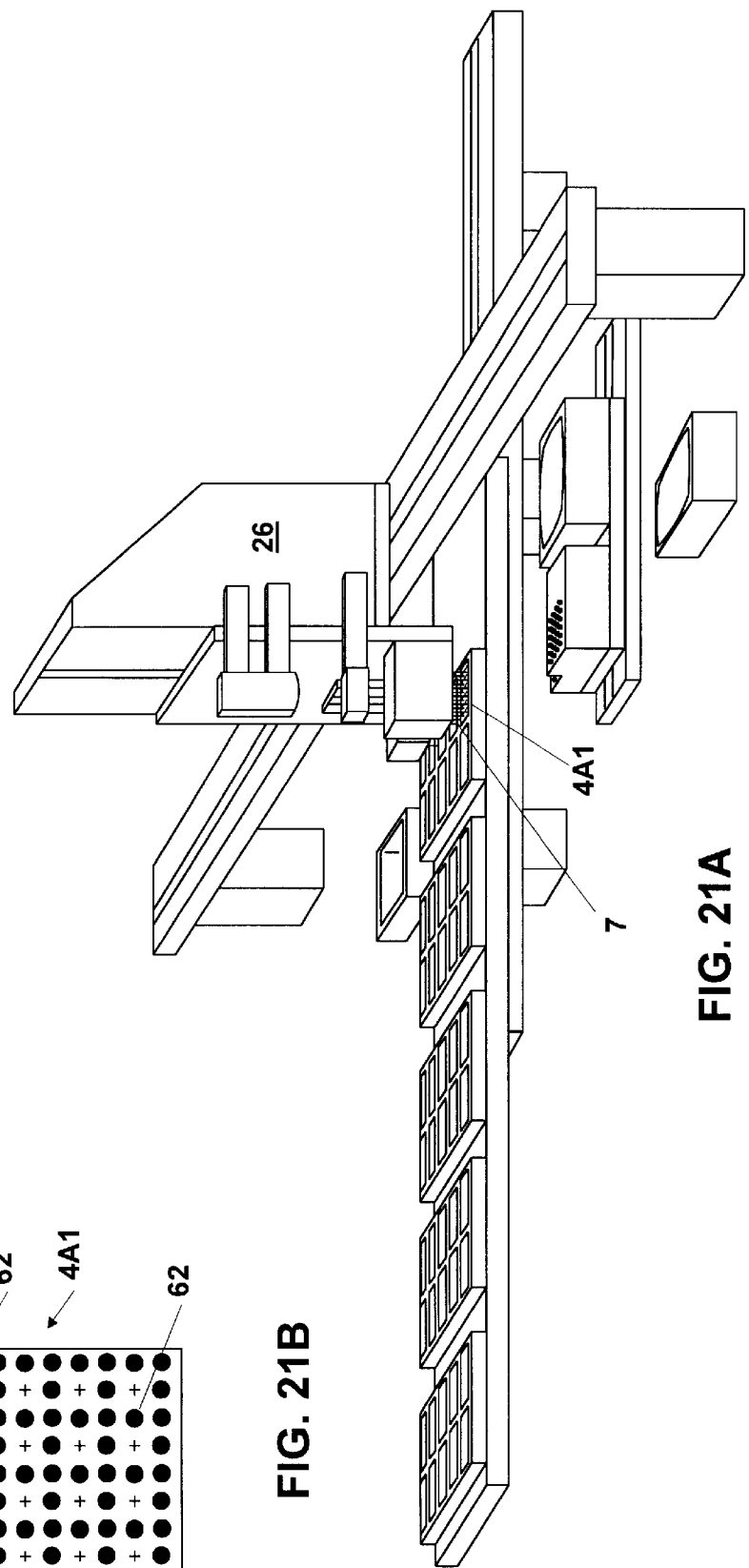
Figure 21B:
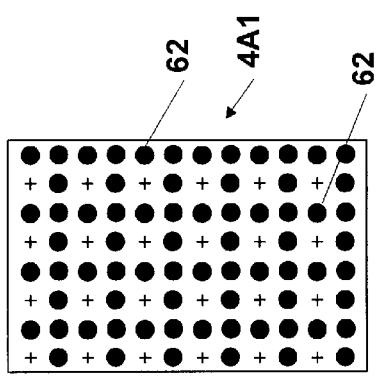

Dispense head 6 is then lowered via linear actuator 26 so that tips 7 are in contact with slide 4A1 at the third dispense position, as shown in FIG. 21A. As tips 7 contact slide 4A1, more liquid spots 62 are added to slide 4A1, as shown in FIG. 21B.

Figure 22:
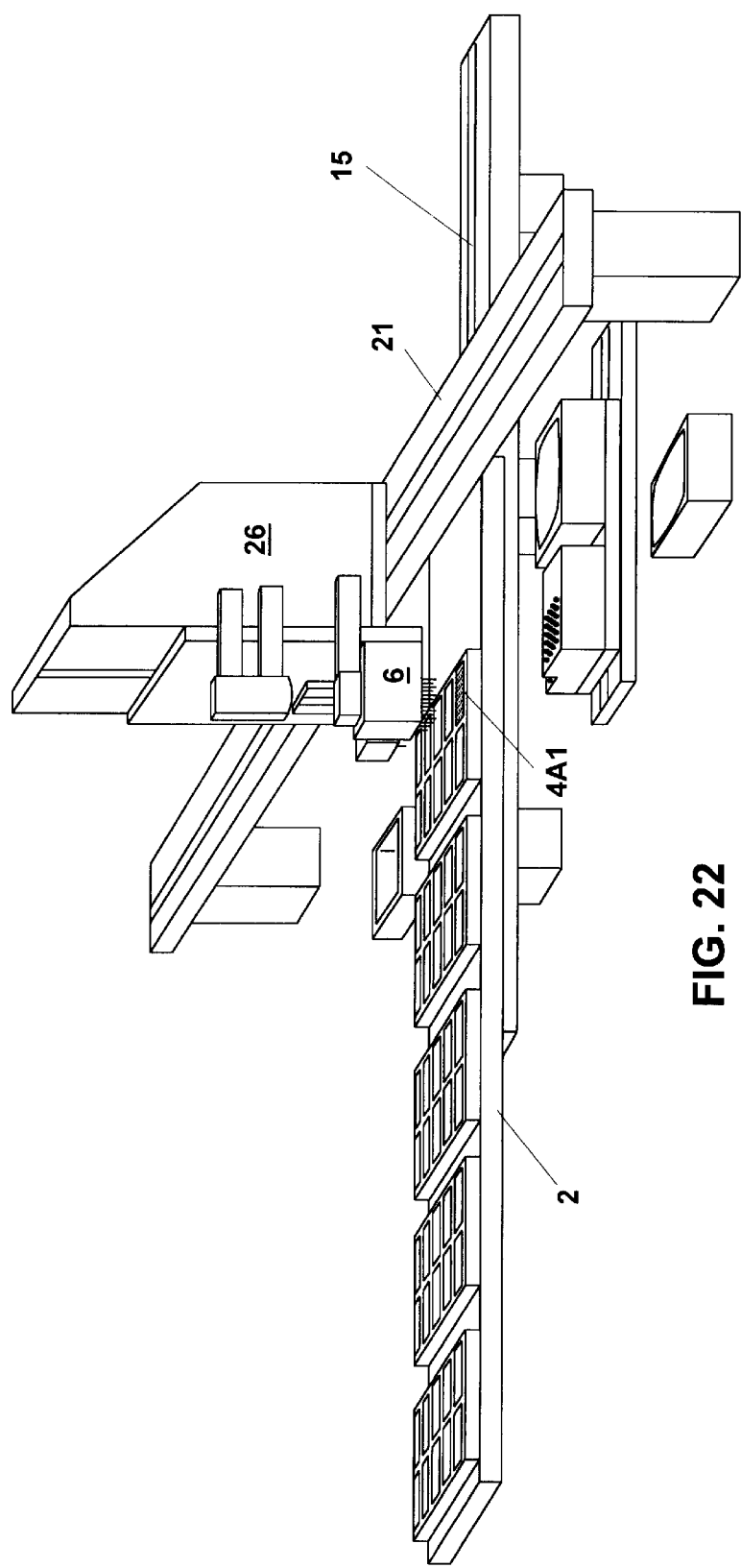

Dispense head 6 is raised via linear actuator 26, as shown in FIG. 22. Based on the earlier positioning data regarding slide 4A1, linear actuator 21 makes minute positioning adjustments to linear actuator 26 and linear actuator 15 makes minute positioning adjustments to platform 2 in order to accurately position dispense head 6 over slide 4A1 at the fourth dispense position.

Figure 23A:
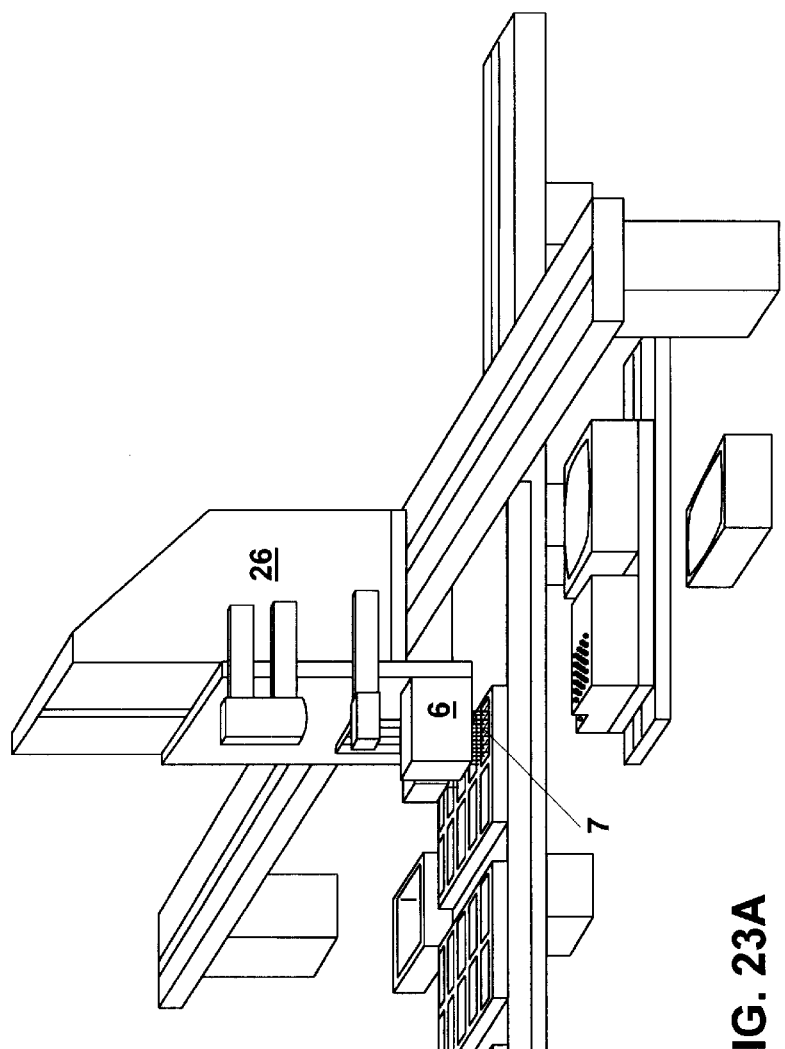
Figure 23B:
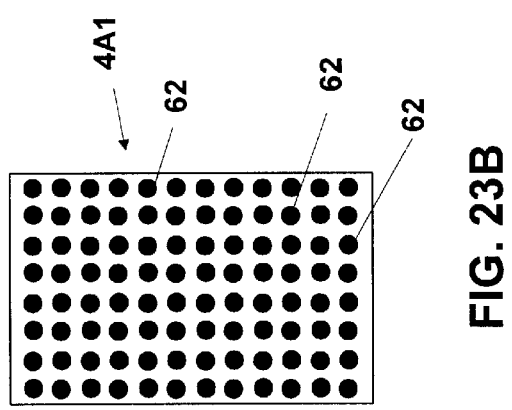

Dispense head 6 is then lowered via linear actuator 26 so that tips 7 are in contact with slide 4A1 at the fourth dispense position, as shown in FIG. 23A. As tips 7 contact slide 4A1, more liquid spots 62 are added to slide 4A1, as shown in FIG. 23B.

Figure 24:
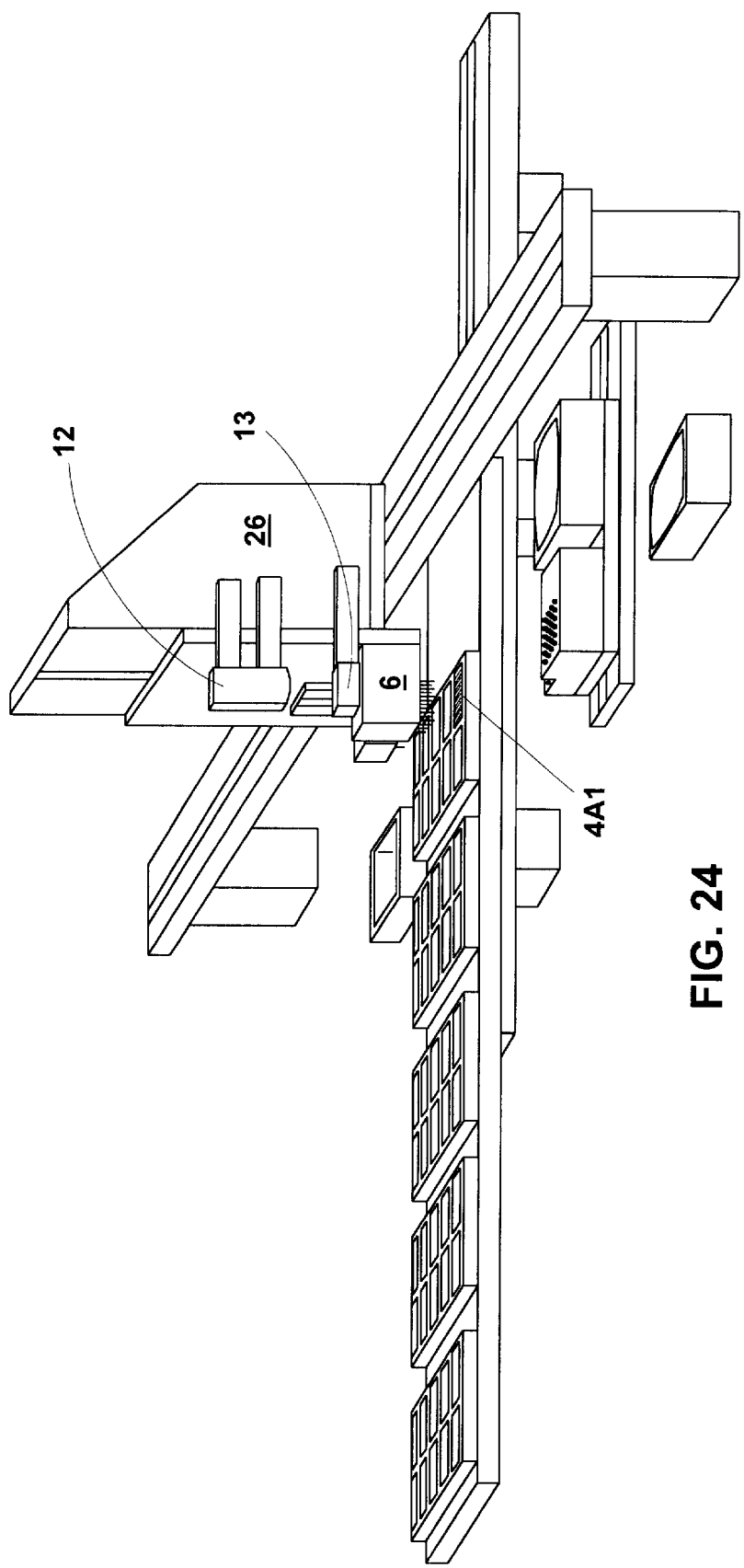

Dispense head 6 is raised via linear actuator 26, as shown in FIG. 24. Camera 12 and strobe 13 scans slide 4A1 and acquires images and inspects for spot quality. It is at this point that PC control system 300 (FIG. 37) identifies slide 4A1 as pass or fail. (Preferred computer controlled techniques for making this determination are discussed in a following section.)

Figure 25:
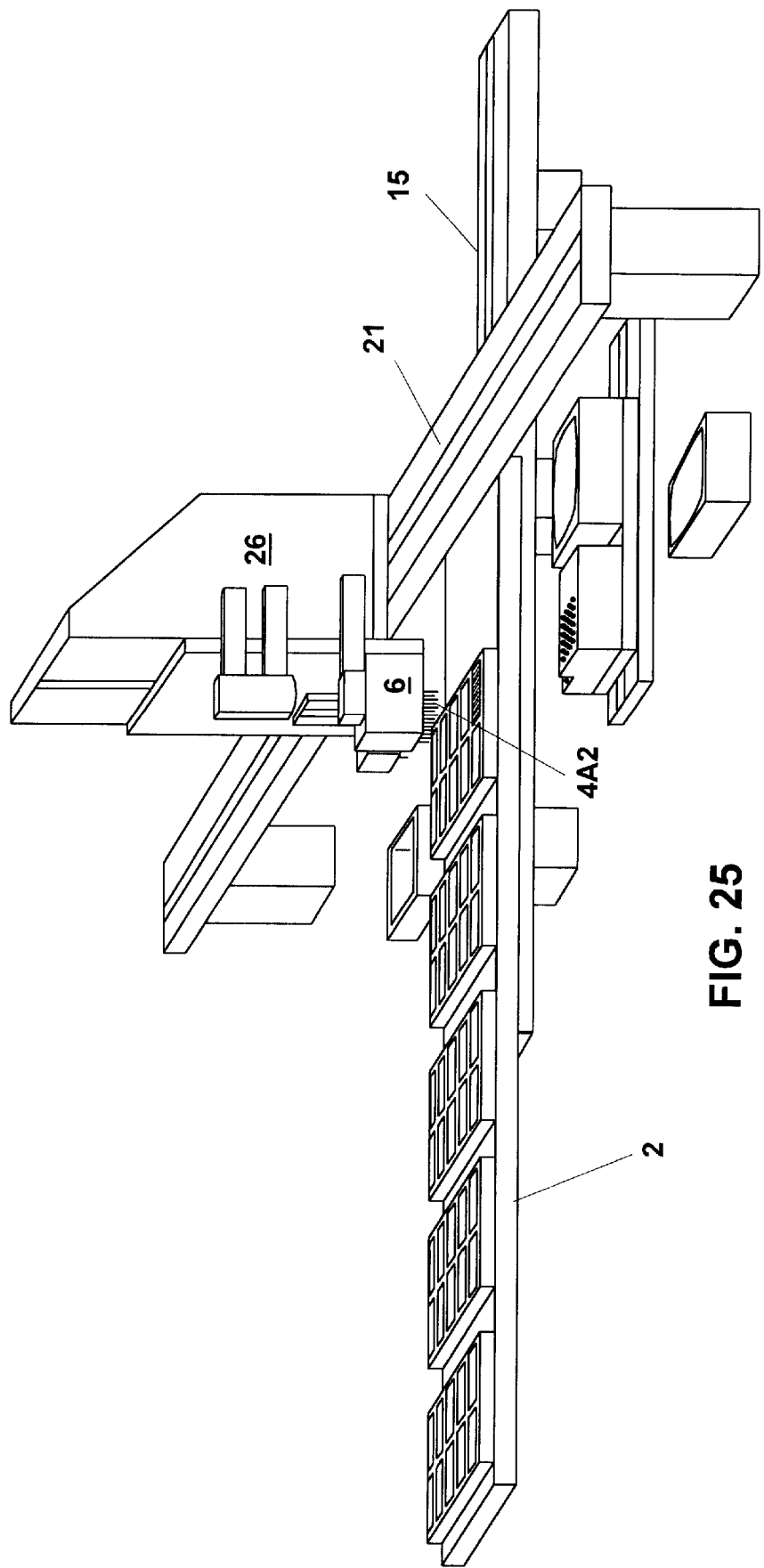

As shown in FIG. 25, based on the earlier positioning data regarding slide 4A2 (see discussion regarding FIG. 5), linear actuator 21 makes positioning adjustments to linear actuator 26 and linear actuator 15 makes positioning adjustments to platform 2 in order to accurately position dispense head 6 over slide 4A2 at the first dispense position for slide 4A2.

Figure 26A:
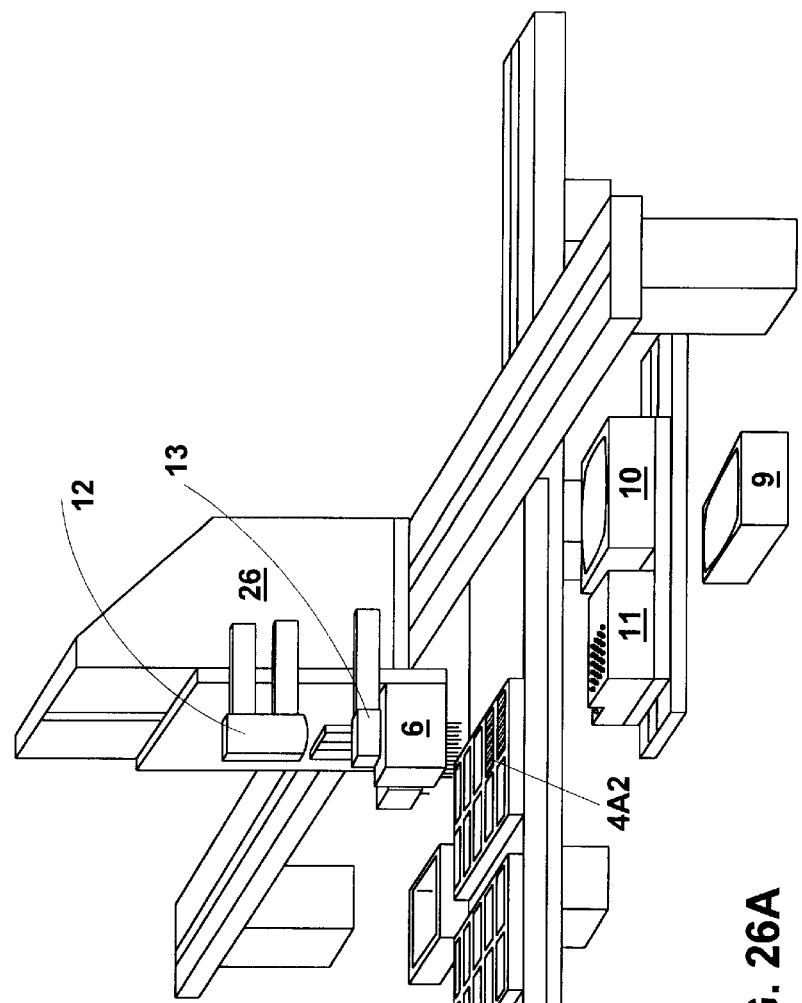
Figure 26B:
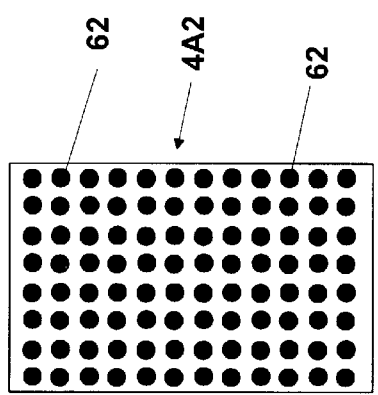

The four-stage liquid dispense cycle (explained above with respect to slide 4A1 in discussion regarding FIGS. 17A–24) is repeated so that at the end of the four-stage cycle, slide 4A2 contains spots 62, as shown in FIG. 26B. At the end of the four stage cycle, dispense head 6 is raised via linear actuator 26, as shown in FIG. 26A. Camera 12 and strobe 13 scans slide 4A2 and acquires images and inspects for spot quality. It is at this point that the control system identifies slide 4A2 as pass or fail.

Figure 27:
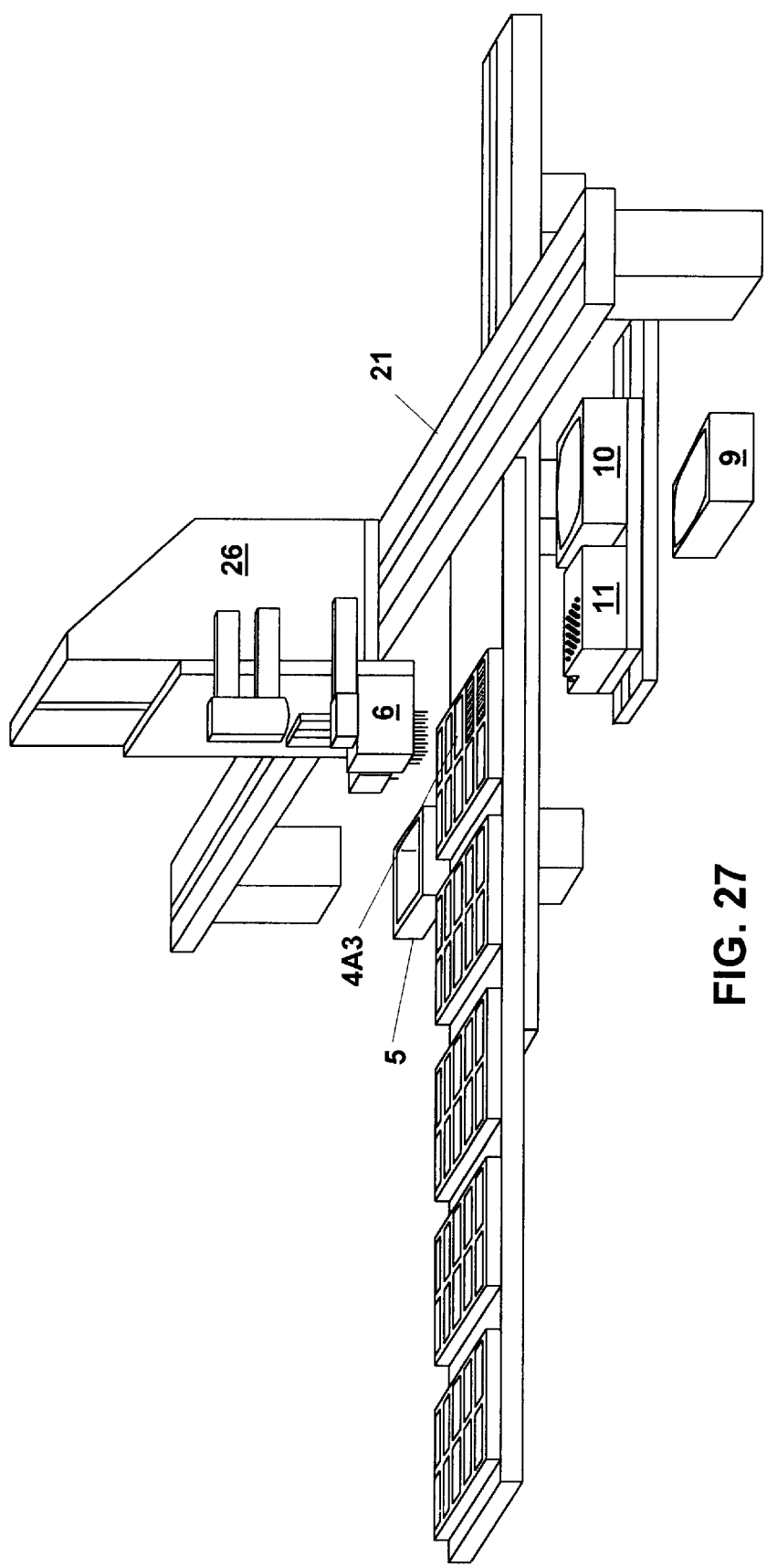

As shown in FIG. 27, linear actuator 21 moves linear actuator 26 so that dispense head 6 is above slide 4A3.

The sequence outlined in the discussion regarding slides 4A1 and 4A2 (depicted in FIGS. 4–26) is repeated with regards to slides 4A3 and 4A4. To summarize, by utilizing light provided by strobe 13, camera 12 will first record the positions of slides 4A3 and 4A4. Then, dispense tips 7 are dipped in sonic cleaner 9. Dispense tips 7 are then rinsed in rinse fountain 10. Then, dispense tips 7 are dried in vacuum manifold 11. This cycle is repeated as needed. Then, liquid is picked up by dispense tips 7 when dispense tips 7 are lowered into reservoir plate 5. Then, liquid is spotted onto slide 4A3 by dispense tips 7 in a four-stage liquid dispense cycle. Likewise, liquid is spotted onto slide 4A4 in a four-stage liquid dispense cycle so that liquid has been spotted on both slides, as shown in FIGS. 28B and 28C.

Figure 29:
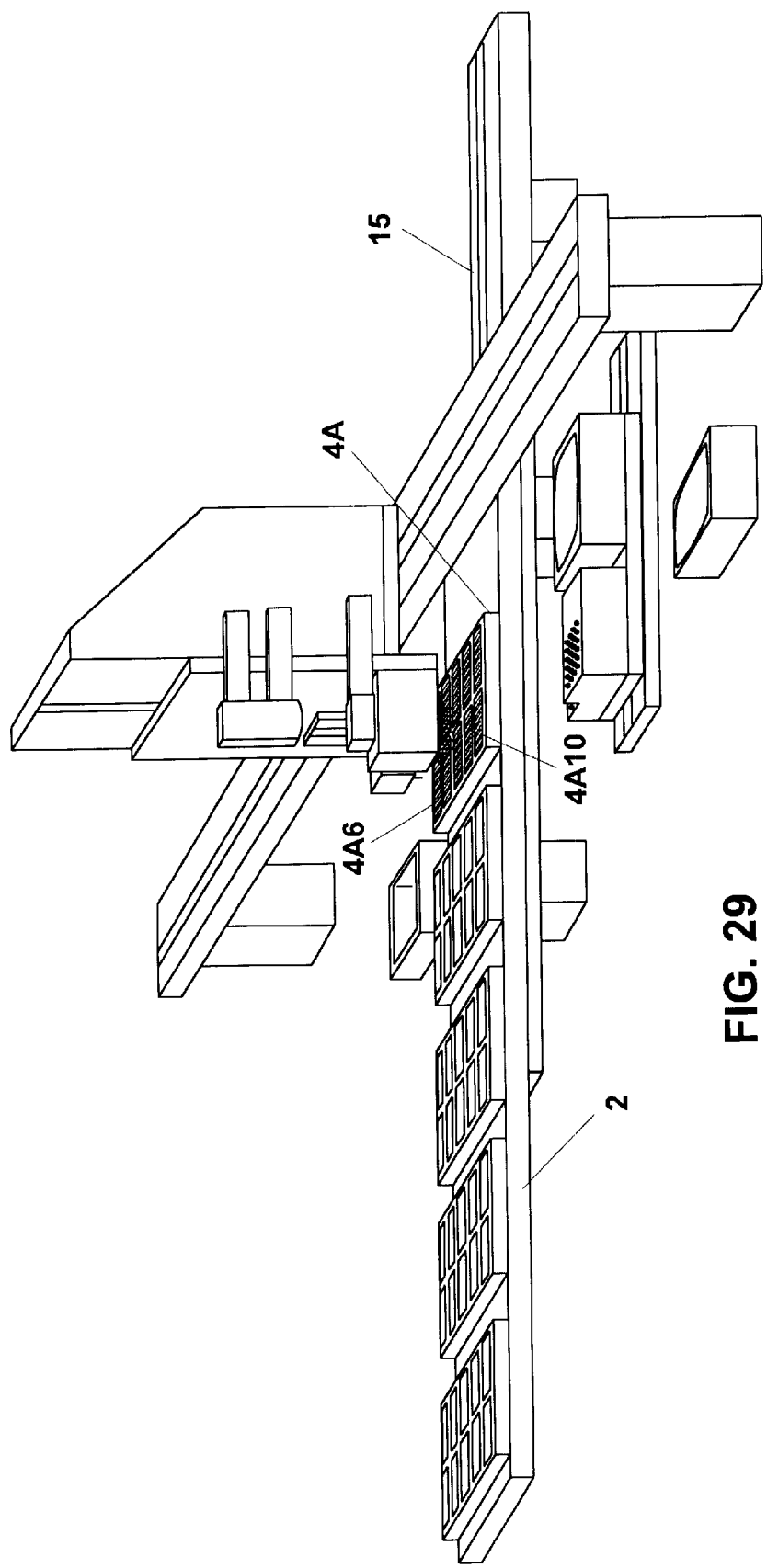

The process is then repeated for the remaining six slides 4A5–4A10 until all the slides on locator plate 4A have been spotted, as shown in FIG. 29.

Figure 30:
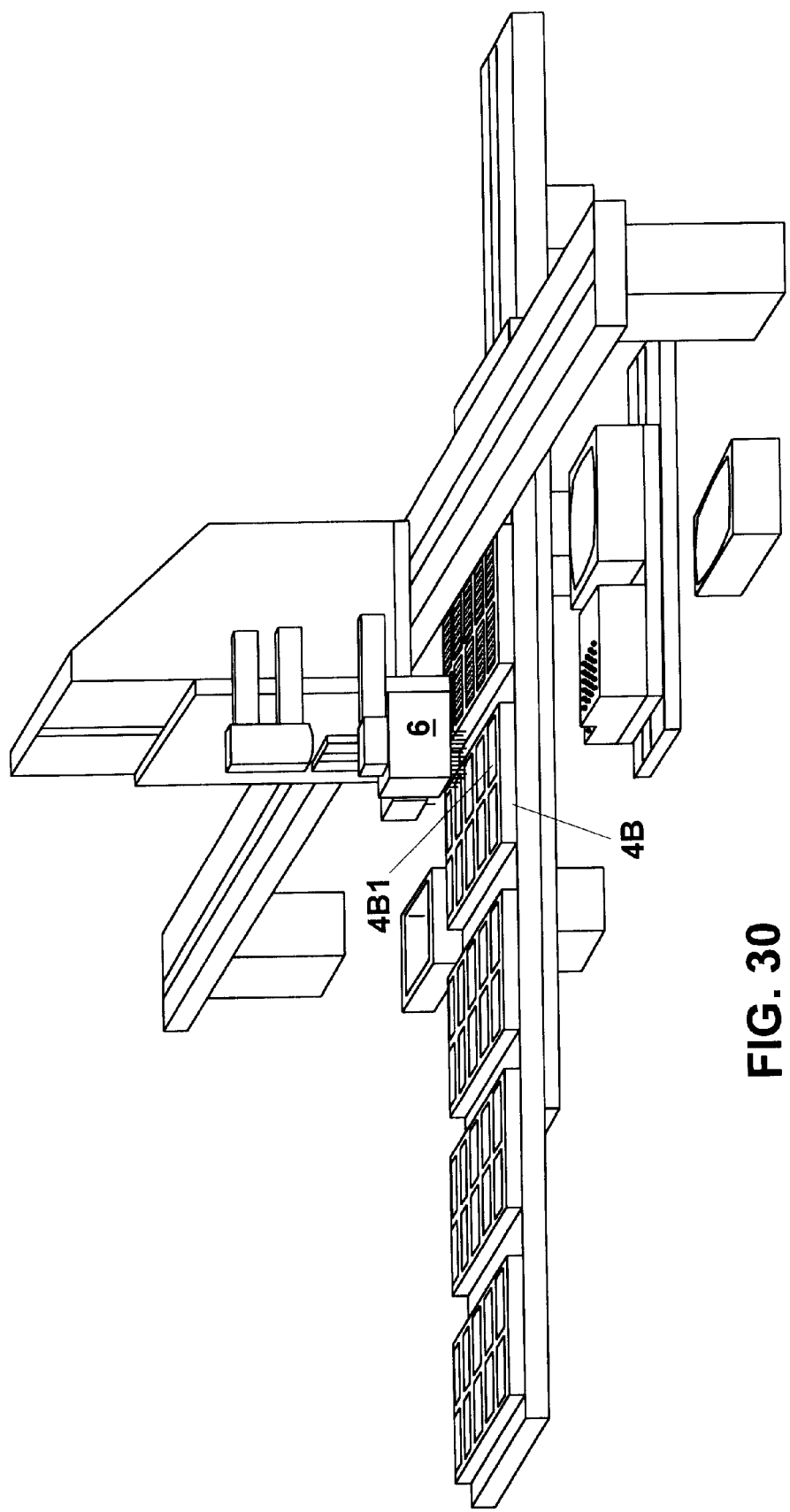

Linear actuator 15 then moves platform 2 so that slide 4B1 of locator plate 4B is underneath dispense head 6, as shown in FIG. 30.

Figure 31:
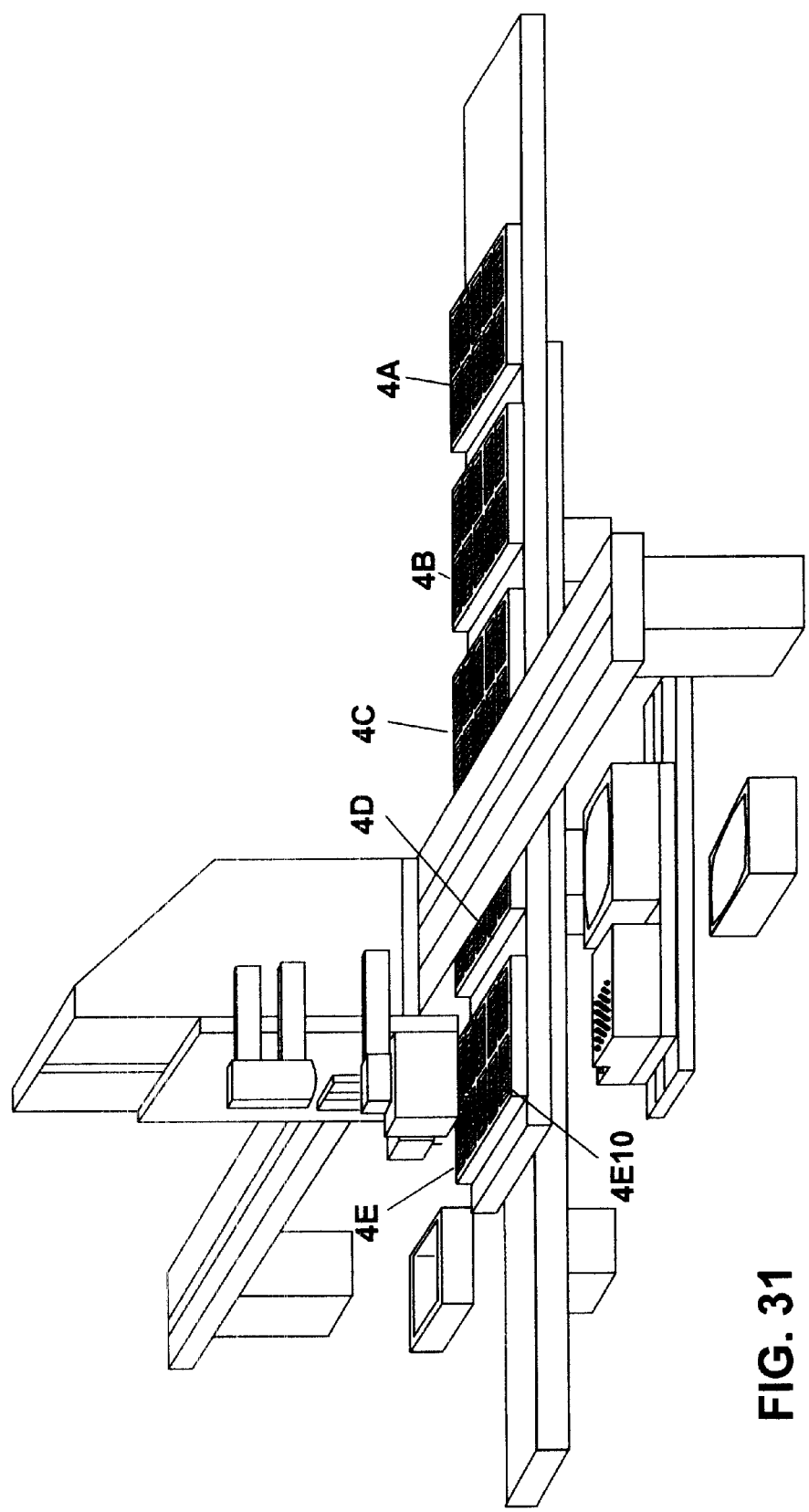

In a similar fashion, dispense tips 7 continue to spot all ten slides on locator plates 4B–4E, until the last slide 4E10 has been spotted, as shown in FIG. 31.

Figure 32:
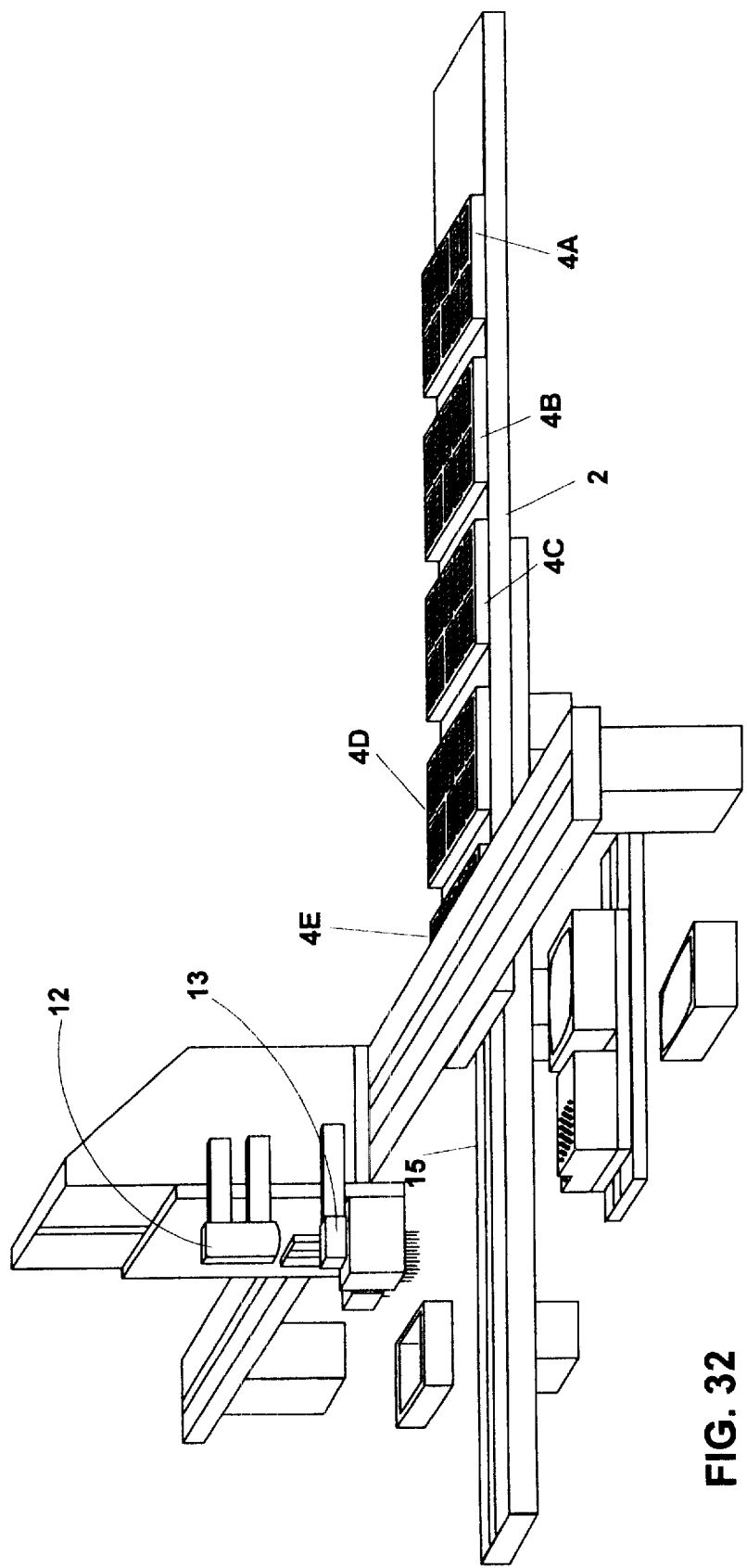

After slide 4E10 has been spotted and camera 12 and strobe 13 has scanned slide 4E10 for spot quality, linear actuator 15 moves platform 2 to the position shown in FIG. 32 so an operator can remove locator plates 4A–4E.

Computer Controlled Pass-Fail Determination Technique

The computer controlled pass-fail determination technique determines individual spots as pass or fail based on several criteria. For each slide, the camera system scans a region to look for a spot. In a preferred embodiment the criteria that are applied to that inspection region are spot presence, spot size in area, spot location, and spot geometry. Additional criteria can be added through software configuration. Each of the criteria can have upper and lower limits designated which define the acceptable values for that particular criteria.

Any value that falls outside of the limits for any criteria qualifies that spot and slide as failed. The actual inspection values are determined by analyzing the grayscale intensity of each pixel. The total number of pixels falling above and below a threshold are tallied to give values for each of the inspection criteria.

Rework Capability

As explained above, after each slide has been spotted, camera 12 and strobe 13 scans the slide and acquires images and inspects for spot quality. It is at this point that the control system identifies the slide as pass or fail. In a preferred embodiment of the present invention, an operator monitoring the spotting process via monitor 305 (FIG. 37) has the option of correcting a slide that has failed.

For example, FIG. 29 shows locating plate 4A after all slides 4A1–4A10 have been spotted. At this point, an operator can scan locating plate 4A. A good plate shows up green as in all slides pass. A plate with at least one bad spot on one of the slides shows up red. The user can then zoom in on the bad slide and the good and bad spots show up green and red respectively as pass or fail. From there, the user can decide whether or not to rework the bad spots.

FIGS. 39A and 39B show where an operator has decided to rework slide 4A6 that has a spot that has failed quality inspection. Dispense head 40 is lowered via pneumatic slide 41 so that dispense tip 42 is lower than dispense tips 7. Solution from reservoir plate 5 is then deposited on the slide at the location of the failed spot. If there are other spots that failed, the operator can likewise rework those spots in a similar fashion.

Although in the description given above regarding the rework process, the operator reworked failed slides after locating plate 4A had been entirely spotted, it is also possible to rework failed slides at other stages during the spotting process. For example, it may be desirable to wait until all slides 4A1–4E10 on plates 4A–4E have been spotted (FIG. 31) before reworking them. This allows an operator to be free to do other activities while the initial spotting is taking place. Then, after all slides have been spotted, he can come back and do all the reworking at one sitting.

Alternatively, it may be desirable to rework each slide immediately after it has been spotted, as shown in FIG. 24.

Automatic Rework Capability

The previous section described a preferred embodiment where an operator can decide whether or not to rework a spot based on a computer determination of pass or fail. In another preferred embodiment the rework decision is made automatically by the computer based on whether or not the spot has passed or failed. In this preferred embodiment, the computer makes a determination whether or not a spot has passed or failed using the computer controlled pass-fail determination technique earlier described. If, based on its analysis, the computer determines that the spot has failed, the computer will automatically take steps to rework the spot. For example, dispense tip 42 will extract solution from reservoir plate 5. Then, the computer will lower dispense head 40 via pneumatic slide 41 so that dispense tip 42 is lower than dispense tips 7, as shown in FIGS. 39A and 39B. Solution from reservoir plate 5 will then deposited on the slide at the location of the failed spot.

Figure 33:
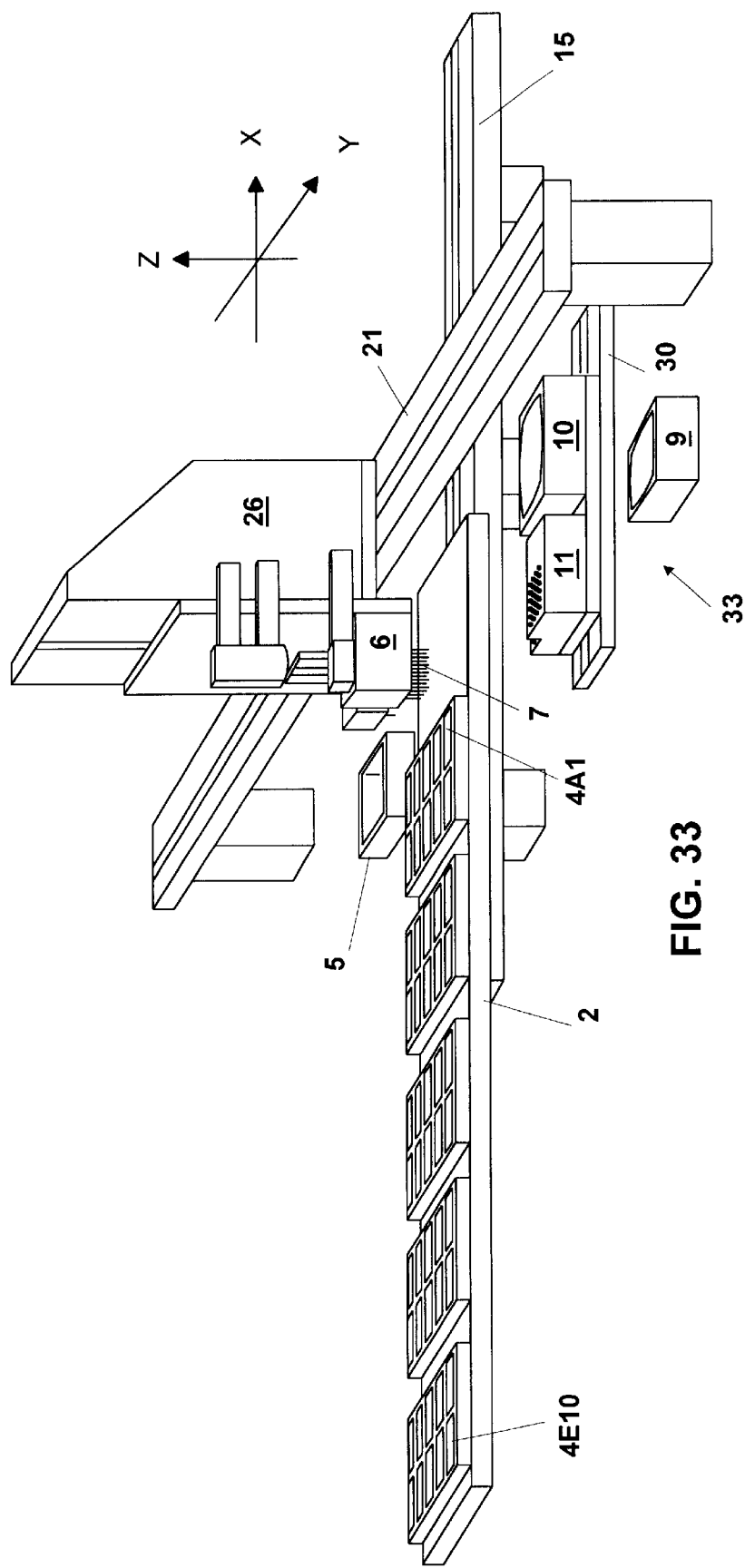
FIG. 33 shows the major components of a preferred embodiment of the present invention.

Components of a Preferred Embodiment of the Present Invention Three Axis Robotic Positioning Stage In a preferred embodiment, linear actuators 26, 21 and 15 are industrial grade precision ground ball screw linear actuators, as shown in FIG. 33. These linear actuators are manufactured by Parker Automation (Model #s:404XR and 406XR series). They are each controlled by a smart servomotor (SmartMotor, Model #2320 VRE, manufactured by Animatics, with offices in Santa Clara Calif.), which is a fully self-contained closed loop servo system. Each of these smart servomotors contains the motor, encoder, amplifier, and controller all in one small package mounted to the linear actuator. Linear actuator 15 (the x-axis positioning device) has an overall travel distance of 600 mm with an accuracy within +/−0.032 micrometers Linear actuator 21 (the y-axis positioning device) has an overall travel distance of 400 mm with an accuracy within +/−0.032 micrometers. Linear actuator 26 (the z-axis positioning device) has an overall travel distance of 100 mm with an accuracy within +/−micrometers. In this preferred embodiment, this extreme accuracy is needed to accommodate very small spot size and spacing between spots. The linear actuators have pitches of 5 mm per revolution giving a positioning accuracy of $0.032 \times 10_{-6}$ meters.

Linear actuator 15 controls the positioning of platform 2 containing slides 4A1–4E10 along the x-axis of motion making all slides presentable to the dispense head 6. Linear actuator 21 controls the positioning of the dispense head along the y-axis of motion making all slides 4A1–4E10, sonic cleaner 9, rinse fountain 10, vacuum manifold 11, and reservoir plate 5 presentable to dispense head 6. Linear actuator 26 controls the positioning of dispense head 6 along the z-axis of motion allowing dispense head 6 to be lowered to and raised from all slides 4A1–4E10, sonic cleaner 9, rinse fountain 10, vacuum manifold 11, and reservoir plate 5.

Cleaning Station

Cleaning station 33 consists of sonic cleaner 9, rinsing fountain 10, and a drying vacuum manifold 11. In a preferred embodiment, sonic cleaner 9 is an ultrasonic cleaner manufactured by Prosonic, Inc. (part no. E0028). Sonic cleaner 9 can contain either a cleaning solution or simply purified water. Dispense tips 7 are dipped in the sonic cleaner 9, where the ultra sonic oscillations of the cleaning solution clean the tips.

Rinsing fountain 10 and the vacuum manifold 11 are placed on a pneumatic slide 30. Pneumatic slide 30 is used to select which operation is to be performed, rinsing or drying. The reason for this slide is so that both operations can be performed at a single position along the y-axis. This allows for both operations without having to increase the overall travel of linear actuator 26 along the y-axis.

Rinsing fountain 10 pumps in purified water and drains it out to a waste bin. Dispense tips 7 are dipped in this purified water to rinse away any debris or cleaning solution that may remain on the tips after cleaning.

Drying vacuum manifold 11 is a block with an array of holes in it that match the array of dispense tips 7. The tips are inserted into the block, each of these holes are connected to a manifold which is connected to a vacuum generator and air supply. The vacuum pulls away any remaining liquid or debris left on the dispense tips after rinsing.

Dispense Head Assemblies

Figure 35B:
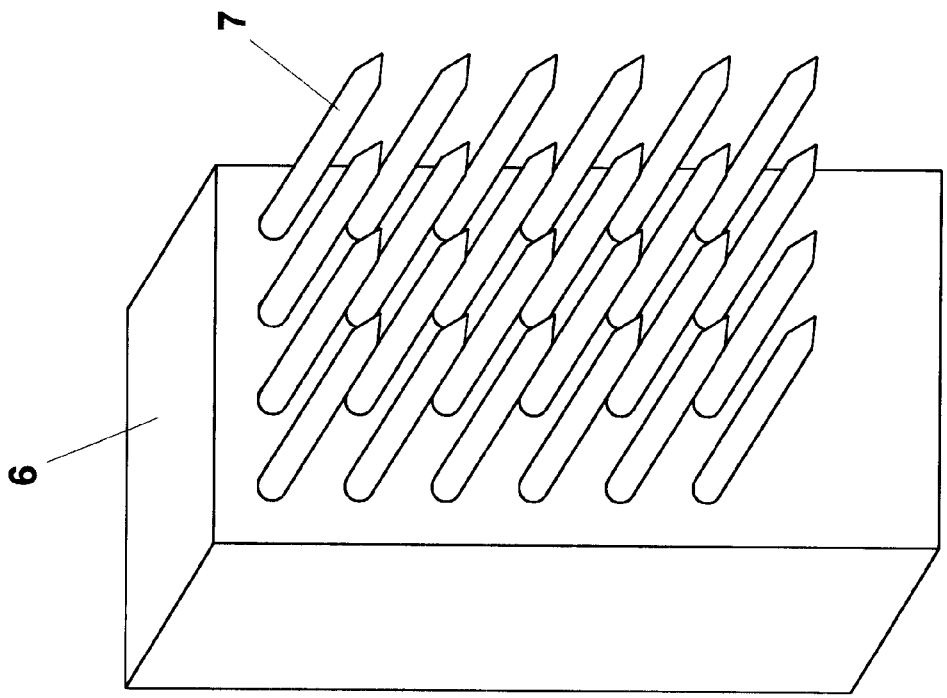
FIGS. 35A and 35B shows dispense tips attached to dispense heads.
Figure 35A:
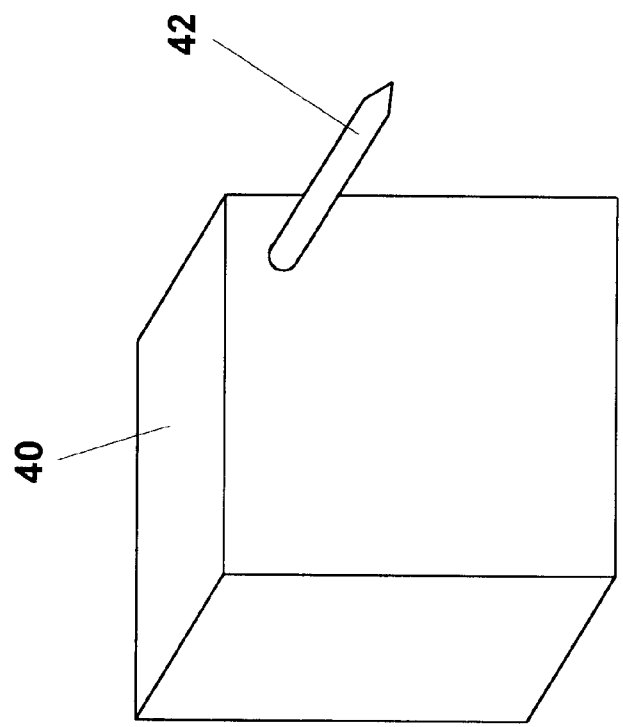

As shown in FIG. 35B, dispense head 6 is a 4×6 grid Micro Quill Holder (part no. 11946-0) made by Major Precision of Arizona. A 4×6 array of primary dispense tips 7 are held in dispense head 6. As shown in FIG. 35A, dispense head 40 is a Micro Quill Holder also made by Major Precision. Dispense tip 42 is held in dispense head 40. Dispense tips 7 and 42 are spring loaded within the dispense heads 6 and 40.

Figure 2:
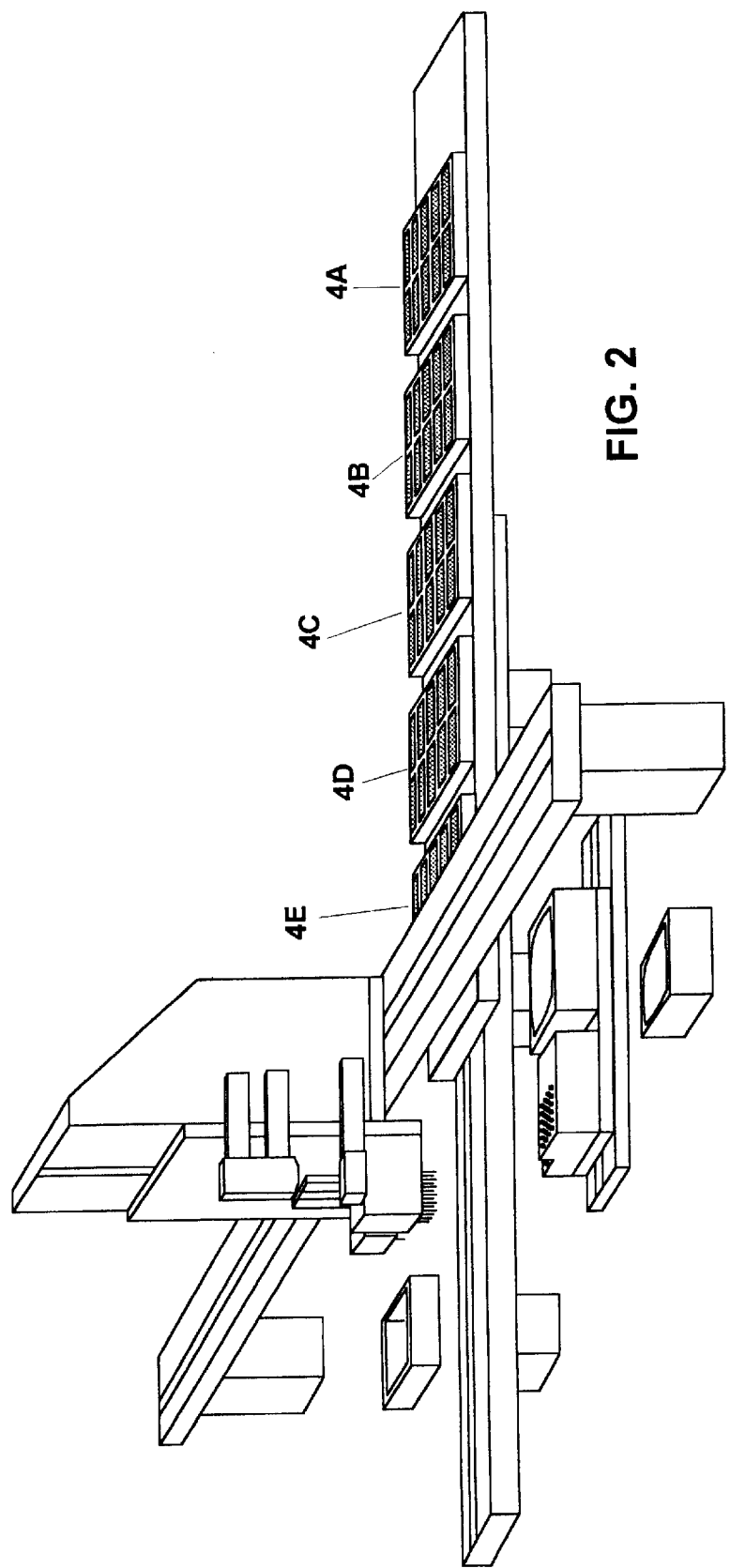
FIG. 2 shows slides fifty slides located on 5 locating plates after the slides have been spotted.

As shown in FIGS. 1, 34A and 34B, dispense head 6 is rigidly mounted to mounting plate 25, whereas dispense head 40 is mounted to pneumatic slide 41 (manufactured by Robohand, Inc., with offices in Montroe, Conn., part no. MPS1-2). Mounting plate 25 is capable of moving up and down along the z-axis via linear actuator 26. Furthermore, dispense head 40 is capable of independent additional movement up and down along the z-axis via pneumatic slide 41, as shown in FIGS. 34A–34B.

During normal operation, such as that depicted in the sequence illustrated in FIGS. 3–32, dispense head 6 is used to spot slides 4A1–4E10. For example, FIG. 34C shows a front view of dispense tips 7 in contact with slide 4A1. Dispense tips 7 will be used to spot slide 4A1 at positions 60, as shown in FIG. 34C. Note that when dispense head 6 has been selected, dispense head 40 is raised via pneumatic slide 41 so that dispense tips 42 do not interfere with the spotting process.

If, however, the operator wishes to spot slide 4A1 at positions 61 (FIG. 34C), dispense head 40 will be lowered via pneumatic slide 41 so that dispense tips 42 are in contact with slide 4A1 and dispense tips 7 are out of the way, as shown in FIG. 34B.

Camera and Lighting

In a preferred embodiment, camera 12 and strobe 13 are mounted to the side of linear actuator 26 as shown in FIG. 1. Camera 12 is a self-contained camera with image processing and Ethernet capabilities manufactured by DVT Corporation with offices in Norcross, Ga. (series 600 model). Using light provided by strobe 13, camera 12 can snap pictures while in dynamic motion, process the image for results, pass the results off to the PC control system, and prepare for the next image acquisition. The camera uses a 55 mm Telecentric lens which provides the proper field of view and magnification for reading of 2D bar code 62 (FIG. 34C) and for image inspection. Strobe light 13 is preferably Model DL2449, manufactured by Advanced Illumination, with offices in Rochester, Vt. In the preferred embodiment, the image acquisition time is ~40 ms and the image processing time is ~50 ms. The system can also be equipped with a flouresence device along with the camera for further genomic expression analysis.

Vibration Isolated Base

Figure 36:
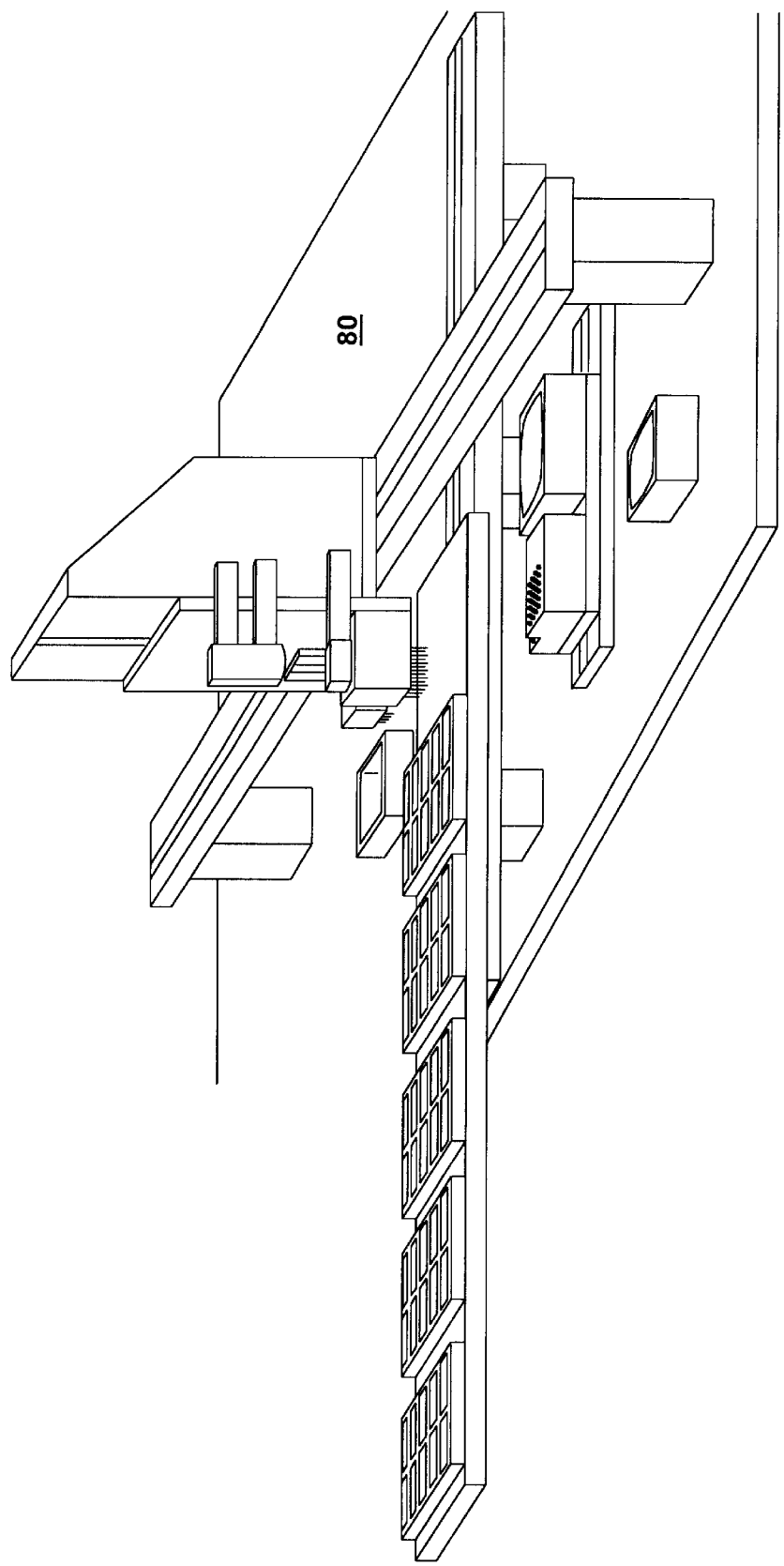
FIG. 36 shows a preferred embodiment of the present invention mounted on a vibration isolated base.
Figure 38A:
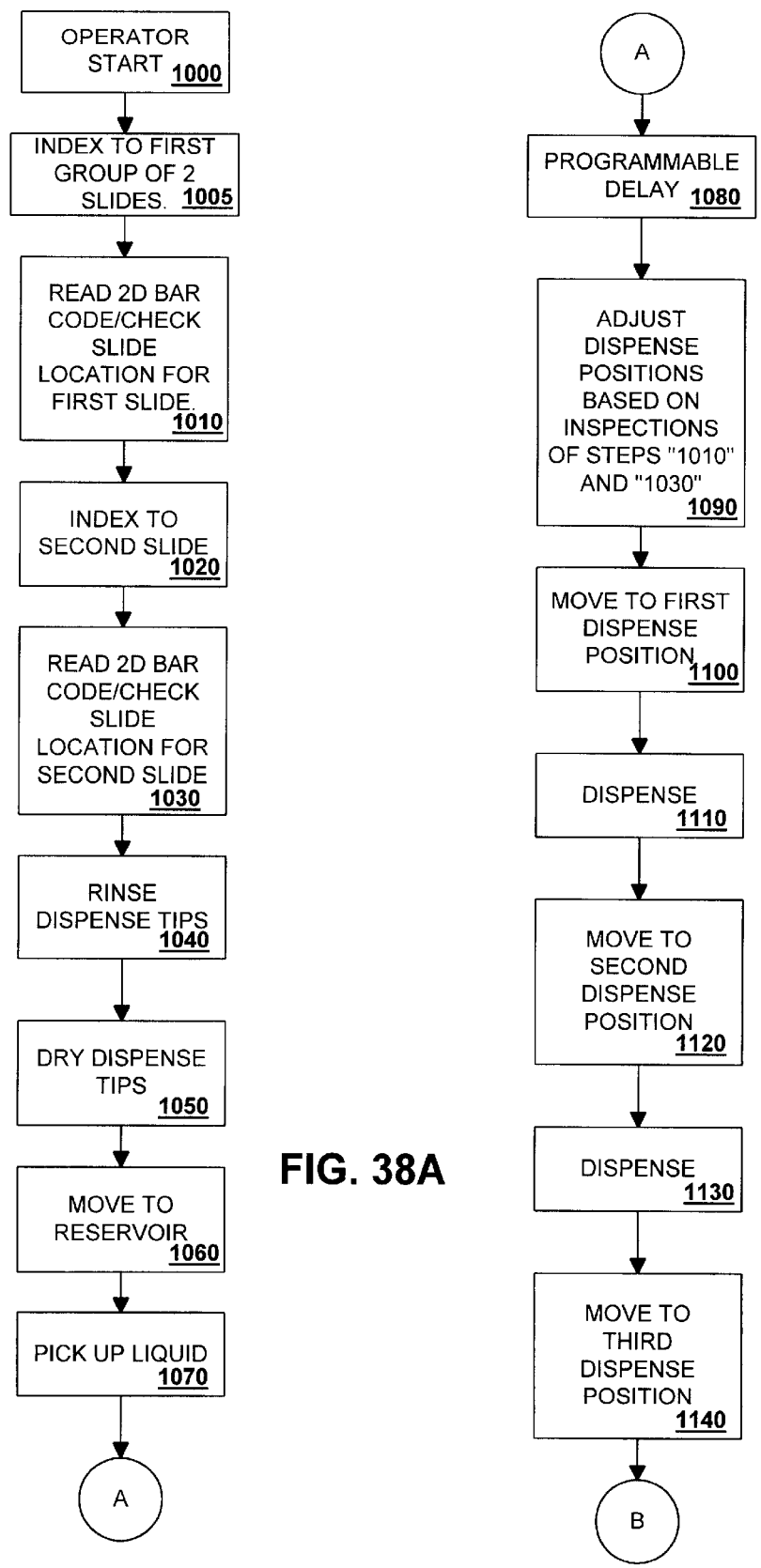
FIGS. 38A and 38B show a flowchart for the programming of a preferred embodiment of the present invention.
Figure 38B:
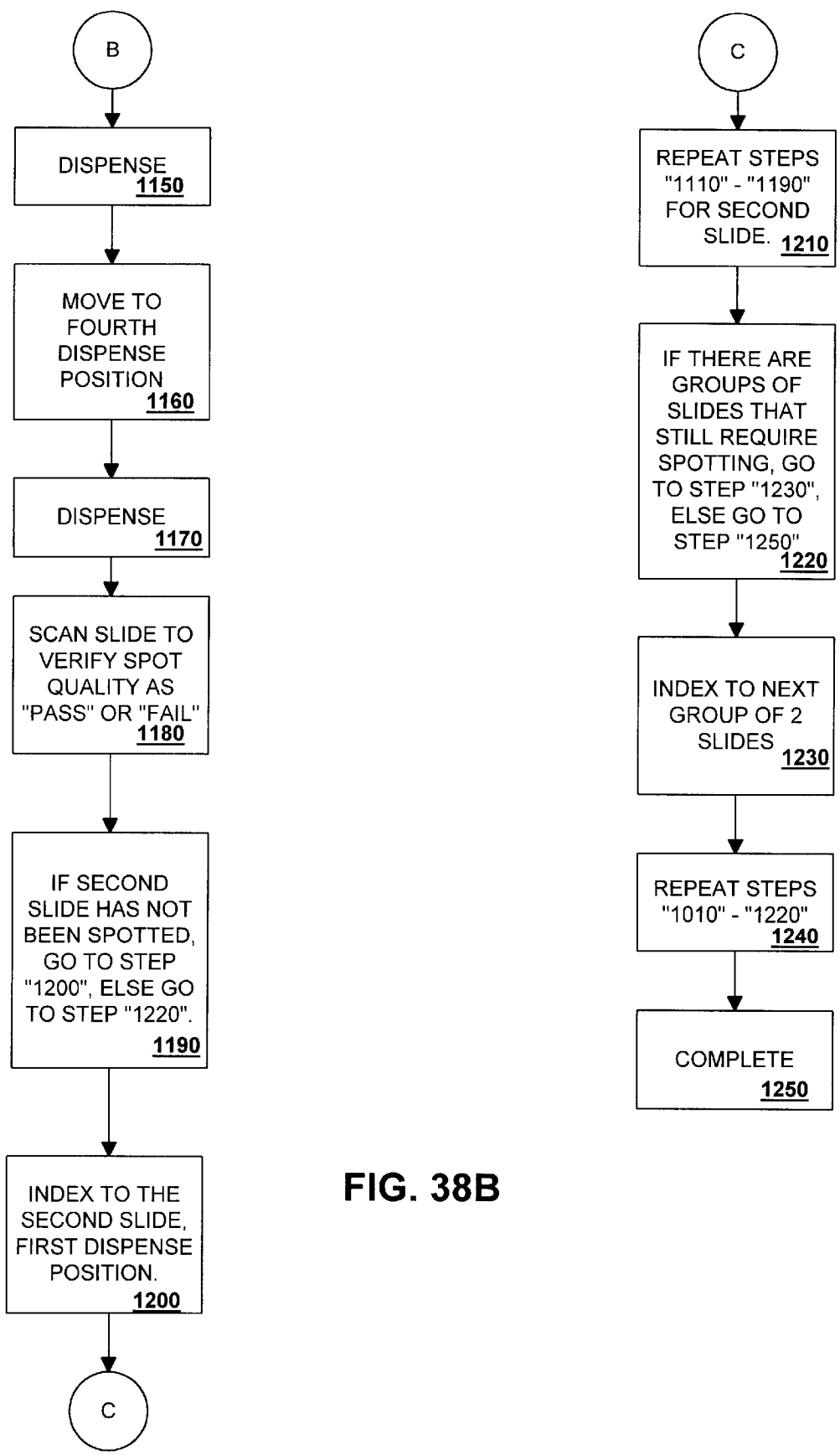

As shown in FIG. 36, vibration isolated base 80 is provided to minimize any possible affects that high frequency environmental vibrations might have on the dispensing process. This base is a pneumatic system which acts as a shock absorber to the system. In a preferred embodiment, the base is manufactured by Newport, Inc. with offices in Irvine, Calif., model #CM-225.

PC Based Control System

FIG. 37 depicts a block diagram of PC control system 300 and other components of a preferred embodiment of the present invention. PC Control System 300 includes CPU 301 with associated memory (RAM 302 and ROM 303). It also includes a touch screen monitor/interface 305 that allows for operator monitoring, intervention and control of the present invention. In the preferred embodiment, the computer system is a PC based computer equipped with an ethernet card and running windows software. The programming is preferably written in VISUAL BASIC. (VISUAL BASIC is a federally registered trademark of Microsoft Corp., a Delaware Corporation) PC Control System 300 is equipped with CMS (Central Monitoring System). The CMS gives PC Control System 300 it's own IP (Internet Protocol) address and ethernet connectivity. This allows for remote monitoring and control via Intranets as well as Internet provided that the bandwith is available for proper functionality. The software is highly comfigurable to allow increased flexibility for customers with varying slide types, slide sizes, slide orientations, spot size, spot spacing and many other variables.

Control of the Components of the Preferred Embodiment of the Present Invention through the PC Control System As previously stated, linear actuators 26, 21 and 15 are industrial grade precision ground ball screw linear actuators. As shown in FIG. 37, PC control system 300 sends signals to smart servomotors 26A, 21A and 15A to control linear actuators 26, 21 and 15, respectively. PC control system 300 controls sonic cleaner 9 and rinse fountain 10. Compressed air source 310 provides compressed air to pneumatic slides 30 and 41 via valves 310 controlled by PC control system 300. Vacuum generator 320 provides a vacuum to vacuum manifold 11 via valve 317. As previously explained camera 12 and strobe 13 work in conjunction to provide sensory data to PC control system 300. This input is used to accurately position the dispense heads over the slides to ensure optimum spotting and to verify the quality of the spotting as "pass" or "fail" using multiple criteria as to placement at intended location as well as spot size (too big or too small).

Second Preferred Embodiment of the Present Invention

Figure 41:
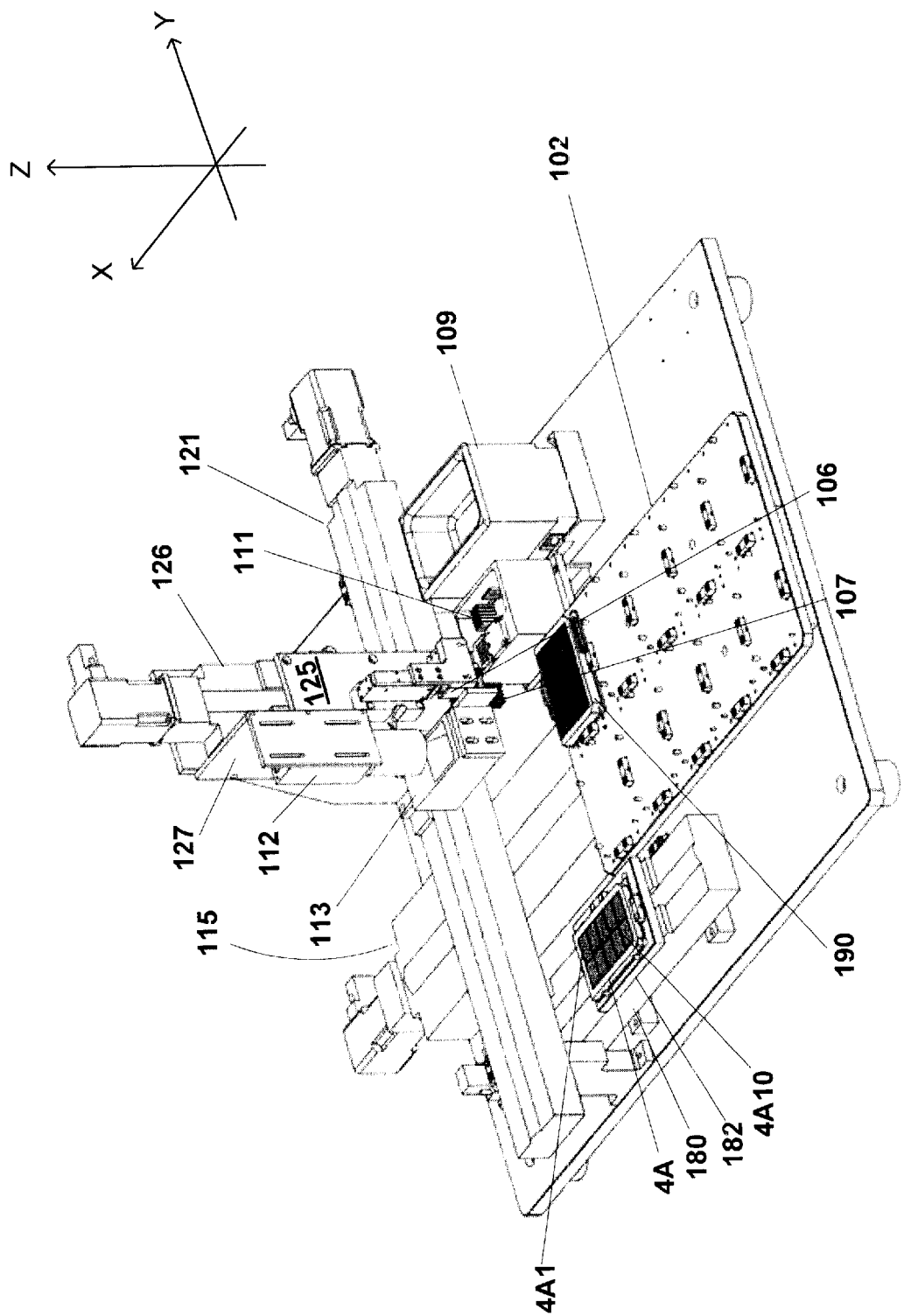
FIG. 41 shows another preferred embodiment of the present invention.

A second preferred embodiment of the present invention is shown in FIG. 41. In the second preferred embodiment, dispense head 106 is connected via mounting plate 125 to linear actuator 126 so that dispense tips 107 can be raised and lowered along the z-axis into solution in microplate 190. Camera 112 and strobe 113 are rigidly mounted to the side of linear actuator 126 so that they remain stationary with respect to the side of linear actuator 126 along the z-axis. Linear actuator 126 is mounted to linear actuator 121 so that it can move along the y-axis.

Platform 182 is mounted to linear actuator 180 so that it can move along the x-axis. Locating plate 4A is placed on top of platform 182. Platform 102 is mounted to linear actuator 115 so that it can move along the x-axis. Microplate 190 is place on top of platform 102. In this preferred embodiment platform 102 has the capacity to hold ten microplates 190.

Solution in microplate 190 is removed via dispense tips 107. Linear actuator 126 then moves along the y-axis so that dispense tips 107 are above locating plate 4A. The solution is then spotted in a fashion similar to that described for the earlier preferred embodiments. Camera 112 with strobe 113 is focused so as to permit recording of the deposition process and functions to permit verification of slide identification information, permit verification of proper deposition of solution on the, slides, and to verify slide alignment. As explained above, slide image data is transferred via camera 112 to a PC control system where the data is analyzed. The results of the analysis are then available for improving the spotting of the solution onto the slides. For example, spots that have failed to meet the threshold limits can be reworked. Also, the computer can automatically make adjustments to the relative positions of the slides and dispense tips based on the slide alignment analysis. Periodically, during the cycle, the dispense tips are cleaned in sonic cleaner 109, then rinsed in the rinse fountain and dried in vacuum manifold 111.

Operation of the First Preferred Embodiment with the Second Preferred Embodiment The first preferred embodiment (described in the sequence illustrated in FIGS. 3–32) can be used in conjunction with the second preferred embodiment to spot slides. For example as shown in FIG. 32, locating plate 4A can be removed from the microarrayer via an operator after it has been spotted with a base solution. Locating plate 4A can be transferred to the microarrayer depicted in FIG. 41. It can be placed on platform 180. DNA from microplate 190 can then be spotted on top of the base solution spotted already on slides 4A1–4A10.

Use of the Present Invention with Other Microarrayers

Although the present invention was described as being used with the preferred microarrayer depicted in the sequence described by reference to FIGS. 3–32, those of ordinary skill in the art will recognize that it is possible to use camera 12, strobe 13 and a PC control system in conjunction with a variety of microarrayer designs. For example, in the background section of this application, several microarrayers were mentioned. It would be possible to one of ordinary skill in the art to modify a prior art automatic microarrayer to include camera 12 and strobe 13. Camera 12 and strobe 13 would then work in conjunction to provide sensory data to PC control system 300, as described above. Also, as explained above, the input would be used to accurately position the dispense heads over the slides to ensure optimum spotting and to verify the quality of the spotting as "pass" or "fail".

Modification of Rework Dispense Tips

Figure 40:
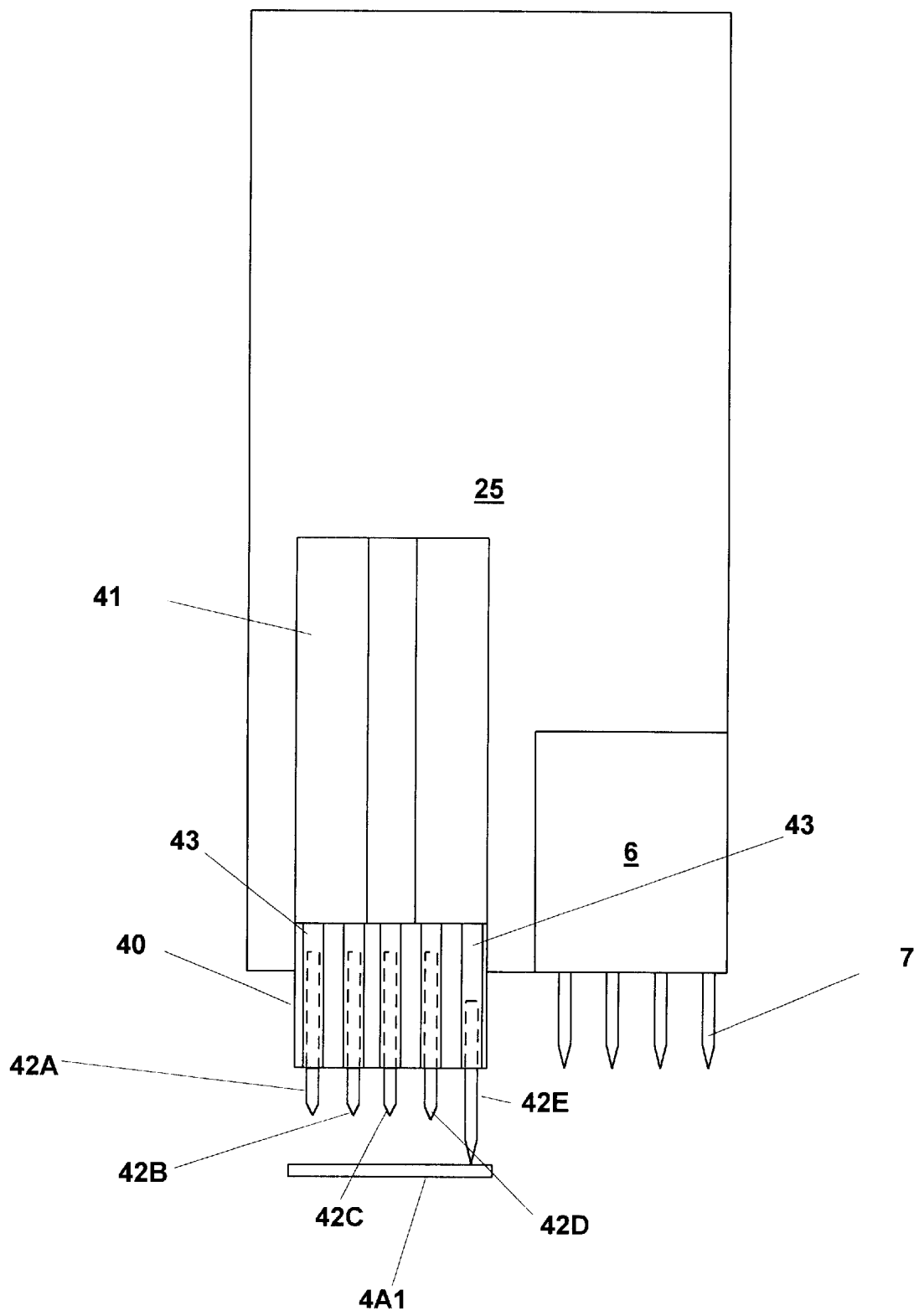
FIG. 40 shows another preferred embodiment of the present invention.

The previous embodiments showed one dispense tip 42 extending downward from dispense head 40. It was explained how the single dispense tip 42 is used for reworking (correcting) defective spots. It is possible, however, to modify dispense head 40 so that multiple dispense tips can extend downward from dispense head 40. A preferred embodiment is shown in FIG. 40 in which five dispense tips 42A–E extend down below dispense head 40. In this preferred embodiment, dispense tips 42A–E are retractably connected to dispense head 40. As shown in FIG. 40, dispense tips 42A–D are retracted inside dispense head 40. The rightmost dispense tip 42E is extended below the other dispense tips and is spotting slide 4A1. In a preferred embodiment, dispense tips 42A–E are mounted to a pneumatic slides 43.

An advantage of this embodiment is that each dispense tip 42 can be configured to dispense a different volume of solution. For example, in a preferred embodiment, dispense tip 42A would dispense 1 nL of solution, dispense tip 42B would dispense 2 nL of solution, dispense tip 42C would dispense 4 nL of solution, dispense tip 42D would dispense 8 nL of solution, and dispense tip 42E would dispense 16 nL of solution.

After initially spotting the slides as explained above, camera 12 and strobe 13 would work in conjunction to provide sensory data to PC control system 300 reporting the quality of the spots. The spots would then be classified as pass or fail. If a spot has failed, the software in conjunction with PC control system 300 would determine the amount of solution required to correct the failed spot. Then, during the reworking sequence, the dispense tip that dispenses the most correct volume would be extended down from dispense head 40 and the other dispense tips would be retracted upward inside dispense head 40, as shown in FIG. 40.

While the above description contains many specifications, the reader should not construe these as limitations on the scope of the invention, but merely as exemplifications of preferred embodiments thereof. Those skilled in the art will envision many other possible variations are within its scope. For example, although the above sequence described a dispensing process utilizing slides that have 96 dispense positions, those of ordinary skill in the art will recognize that it is possible to use other slides as well. For example, 384 or 1536 position slides could be used. It is also possible to use a blank microscope slide with no pre-etched dispense positions. Accordingly, the location of the different dispense positions will vary depending on the type of slide being used. The spacing and orientation of the slide can be selected by an operator through the maintenance menu on the computer interface. Also, the previous embodiments disclosed using a strobe light to illuminate the slide below the camera. One of ordinary skill in the art will recognize that it is possible to illuminate the slide with other light sources besides a strobe light. For example, the slide could be illuminated with a camera flash, a constant bright light, or a fluorescence device, such as a fluorescent LED. If a fluorescence device is used to illuminate the slide, those of ordinary skill in the art will recognize that it is possible to add a fluorescent dye to the solution being spotted to achieve more in depth characterizations. For example, by using a fluorescent LED and adding fluorescent dye to the solution, greater volume determination can be achieved based on fluorescent intensity of the spot. Also, in the preferred embodiment, it was mentioned that dispense tips 7 and 42 were quill type dispense tips, it would be obvious to substitute other types of dispense tips. For example, piezo type dispense tips could also be used. Accordingly the reader is requested to determine the scope of the invention by the appended claims and their legal equivalents, and not by the examples which have been given.

We claim:

1. A microarrayer for spotting solution onto slides, comprising:
   A) at least one dispense head for spotting the slides,
   B) at least one light source capable of illuminating the slides,
   C) at least one camera operating in conjunction with said at least one light source, said at least one camera capable of acquiring and transmitting slide image data,
   D) a computer programmed to:
      1) receive said slide image data from said at least one camera,
      2) analyze said slide image data, and
      3) generate post analysis data based on said analysis of said slide image data, wherein said post analysis data comprises information relating to the success or failure of said microarrayer to successfully spot solution onto the slides and
   E) an adjustment means for permitting adjustments to be made to said spotting of solution onto the slides, wherein said adjustments are based on said post analysis data.

2. The microarrayer as in claim 1, wherein said adjustment means is an automatic adjustment means for permitting said computer to automatically make said adjustments to said spotting of solution onto said slides.

3. The microarrayer as in claim 1, wherein said slide image data comprises information relating to slide alignment.

4. The microarrayer as in claim 1, wherein said slide image data comprises information relating to spot quality.

5. The microarrayer as in claim 4, wherein said post analysis data comprises information reporting the spot quality as pass or fail.

6. The microarrayer as in claim 5, wherein said adjustment means is a reworking means for permitting the microarrayer operator to rework a failed spot via the microarrayer based on said report of said post analysis data.

7. The microarrayer as in claim 5, wherein said adjustment means is a reworking means for permitting said computer to rework a failed spot via the microarrayer based on said report of said post analysis data.

8. The microarrayer as in claim 1, wherein said slide image data comprises slide identification information.

9. The microarrayer as in claim 8, wherein said slide identification information is contained in the slide's 2D bar code.

10. The microarrayer as in claim 1, wherein said slide image data comprises:
    A) information relating to slide alignment,
    B) information relating to spot quality, and
    C) slide identification information.

11. The microarrayer as in claim 1, further comprising a three axis robotic positioning stage for presentation of the slides and said at least one dispense head.

12. The microarrayer as in claim 11, wherein said three axis robotic positioning stage comprises three linear actuators.

13. The microarrayer as in claim 1, further comprising at least one cleaning station, comprising:
    A) a sonic cleaner,
    B) a rinsing fountain, and
    C) a vacuum manifold.

14. The microarrayer as in claim 1, wherein said at least one dispense head is two dispense heads, wherein the first of said two dispense heads is a main dispense head, wherein the second of said two dispense heads is a rework dispense head.

15. The microarrayer as in claim 14, further comprising a dispense head assembly, comprising:
    A) a mounting plate attached to the microarrayer via a linear actuator,
    B) a pneumatic slide mounted to said mounting plate, wherein said main dispense head is mounted to said mounting plate and wherein said rework dispense head is mounted to said pneumatic slide enabling said rework dispense head to move above or below said main dispense head.

16. The microarrayer as in claim 1, wherein said camera is a CCD camera comprising a C-mount lens capable of providing the proper field of view and magnification for reading of the slides' 2D bar code and for acquiring said slide image data.

17. The microarrayer as in claim 1, further comprising a vibration isolated base pneumatically isolated from the microarrayer, wherein said vibration isolated base assists in absorbing the shock of external vibrations.

18. The microarrayer as in claim 1, wherein said computer comprises:
  A) a PC based controller comprising VISUAL BASIC programming, and
  B) a touch screen monitor for user interface.

19. The microarrayer as in claim 1, wherein said computer is capable of being connected to a computer network for remote monitoring and control.

20. The microarrayer as in claim 1, wherein further comprising at least one dispense tip attached to said at least one dispense head.

21. The microarrayer as in claim 1, wherein said at least one dispense tip is a quill type dispense tip.

22. The microarrayer as in claim 1, wherein said at least one dispense tip is a piezo type dispense tip.

23. The microarrayer as in claim 1, wherein said at least one light source is a strobe light.

24. The microarrayer as in claim 1, wherein said at least one light source is a fluorescence device.

25. A microarrayer for spotting solution onto slides, comprising:
  A) a dispensing means for spotting the slides,
  B) a light source means for illuminating the slides,
  C) an image acquisition means for operating in conjunction with said light source means for acquiring and transmitting slide image data,
  D) a computer programmed to:
    1) receive said slide image data from said image acquisition means,
    2) analyze said slide image data, and
    3) generate post analysis data based on said analysis of said slide image data, wherein said post analysis data comprises information relating to the success or failure of said microarrayer to successfully spot solution onto the slides and
  E) an adjustment means for permitting adjustments to be made to said spotting of solution onto the slides, wherein said adjustments are based on said post analysis data.

* * * * *